(12) United States Patent
Bonde et al.

(10) Patent No.: US 12,137,932 B2
(45) Date of Patent: Nov. 12, 2024

(54) MEDICAL ASSEMBLIES AND METHODS FOR IMPLANTATION OF MULTIPLE MEDICAL LEADS THROUGH A SINGLE ENTRY

(71) Applicant: MEDTRONIC, INC., Minneapolis, MN (US)

(72) Inventors: Eric H. Bonde, Minnetonka, MN (US); Phillip C. Falkner, Minneapolis, MN (US); John B. Horrigan, Beverly, MA (US); Stuart R. MacDonald, Andover, MA (US); Madeline A. Mannion, Beverly, MA (US)

(73) Assignee: Medtronic, Inc., Minneapolis, MN (US)

( * ) Notice: Subject to any disclaimer, the term of this patent is extended or adjusted under 35 U.S.C. 154(b) by 603 days.

(21) Appl. No.: 17/008,183

(22) Filed: Aug. 31, 2020

(65) Prior Publication Data
US 2021/0052295 A1 Feb. 25, 2021

Related U.S. Application Data

(62) Division of application No. 13/525,560, filed on Jun. 18, 2012, now Pat. No. 10,758,262.
(Continued)

(51) Int. Cl.
*A61B 17/34* (2006.01)
*A61N 1/05* (2006.01)
(Continued)

(52) U.S. Cl.
CPC ...... *A61B 17/3401* (2013.01); *A61B 17/3468* (2013.01); *A61N 1/0551* (2013.01);
(Continued)

(58) Field of Classification Search
CPC .... A61N 1/0551; A61N 1/05; A61N 1/36017; A61N 1/0553; A61B 17/3468;
(Continued)

(56) References Cited

U.S. PATENT DOCUMENTS 701,075 A 5/1902 McCully
3,144,868 A 8/1964 Jascalevich
(Continued)

FOREIGN PATENT DOCUMENTS

EP 232994 12/1990
WO 20005/023359 3/2005

*Primary Examiner* — Dianne Dornbusch
(74) *Attorney, Agent, or Firm* — Shumaker & Sieffert, P.A.

(57) ABSTRACT

Assemblies and methods provide for implantation of multiple medical leads to a defined space within the body, such as the epidural space, through a single entry. A catheter having multiple lumens or alternatively a single oblong lumen may be used. A distal end of the catheter enters the defined space through the single entry such that the distal ends of the multiple lumens or the oblong lumen are present in the defined space. Medical leads are introduced through the multiple lumens or the oblong lumen into the defined space. In some cases, the distal end of the catheter may be deflectable to direct the medical leads within the defined space. In other cases, sheaths may be present within each lumen of the catheter where the sheaths may be extended into the defined space and deflect to direct the medical leads that are being passed through a lumen of the sheaths.

13 Claims, 39 Drawing Sheets

Related U.S. Application Data

(60) Provisional application No. 61/498,906, filed on Jun. 20, 2011, provisional application No. 61/498,914, filed on Jun. 20, 2011.

(51) Int. Cl.
    *A61B 17/22*     (2006.01)
    *A61M 25/00*     (2006.01)
    *A61M 25/01*     (2006.01)

(52) U.S. Cl.
    CPC ............. *A61B 2017/22021* (2013.01); *A61M 25/0068* (2013.01); *A61M 25/0102* (2013.01)

(58) Field of Classification Search
    CPC ..... A61B 17/3401; A61B 2017/22021; A61M 25/001; A61M 25/003; A61M 25/0041; A61M 25/0102; A61M 25/0067; A61M 2025/0034; A61M 2025/007; A61M 2025/0063; A61M 25/0068
    See application file for complete search history.

(56) References Cited

U.S. PATENT DOCUMENTS

| | | | |
|---|---|---|---|
| 3,495,595 A | 2/1970 | Soper | |
| 3,804,097 A | 4/1974 | Rudie | |
| 4,072,153 A | 2/1978 | Swartz | |
| 4,141,365 A * | 2/1979 | Fischell | A61N 1/0551 |
| | | | 600/377 |
| 4,203,436 A | 5/1980 | Grimsrud | |
| 4,405,313 A | 9/1983 | Sisley | |
| 4,808,157 A * | 2/1989 | Coombs | A61B 17/3401 |
| | | | 604/512 |
| 4,958,901 A | 9/1990 | Coombs | |
| 5,084,013 A | 1/1992 | Takase | |
| 5,167,220 A | 12/1992 | Brown | |
| 5,197,976 A | 3/1993 | Herweck | |
| 5,255,691 A * | 10/1993 | Otten | A61N 1/0551 |
| | | | 607/117 |
| 5,286,253 A | 2/1994 | Fucci | |
| 5,318,517 A | 6/1994 | Reiman | |
| 5,318,530 A | 6/1994 | Nelson, Jr. | |
| D353,454 S | 12/1994 | Coombs | |
| D367,324 S | 2/1996 | McCarthy | |
| D371,732 S | 7/1996 | Owens | |
| 5,558,634 A | 9/1996 | Mitchell | |
| 5,599,304 A | 2/1997 | Shaari | |
| 5,666,619 A | 9/1997 | Zarate | |
| 5,709,224 A * | 1/1998 | Behl | A61B 18/1492 |
| | | | 606/49 |
| 5,752,939 A | 5/1998 | Makoto | |
| 5,782,795 A | 7/1998 | Bays | |
| 5,785,686 A | 7/1998 | Runge | |
| 5,807,311 A | 9/1998 | Palestrant | |
| 5,846,219 A | 12/1998 | Vancaillie | |
| 5,858,009 A | 1/1999 | Jonkman | |
| 5,891,111 A | 4/1999 | Ismael | |
| 6,152,909 A | 11/2000 | Bagaoisan | |
| 6,179,776 B1 | 1/2001 | Adams | |
| 6,214,016 B1 | 4/2001 | Williams et al. | |
| 6,309,401 B1 | 10/2001 | Redko et al. | |
| 6,512,958 B1 | 1/2003 | Gerber et al. | |
| 6,524,302 B2 | 2/2003 | Kelley | |
| 6,755,812 B2 | 6/2004 | Peterson et al. | |
| 6,758,854 B1 | 7/2004 | Butler | |
| 6,836,687 B2 * | 12/2004 | Kelley | A61M 25/0138 |
| | | | 607/116 |
| 6,902,547 B2 * | 6/2005 | Aves | A61N 1/0551 |
| | | | 606/108 |
| 7,014,626 B2 | 3/2006 | Sanderson | |
| 7,089,040 B2 | 8/2006 | McGuckin, Jr. | |
| 7,359,755 B2 | 4/2008 | Jones et al. | |
| 7,381,204 B2 | 6/2008 | Wilson et al. | |
| 7,384,422 B2 | 6/2008 | Worley et al. | |
| 7,455,666 B2 | 11/2008 | Purdy | |
| 7,553,307 B2 | 6/2009 | Bleich | |
| 7,662,128 B2 | 2/2010 | Salcudean et al. | |
| 7,666,204 B2 | 2/2010 | Thornton et al. | |
| 7,717,899 B2 | 5/2010 | Bowe et al. | |
| 7,738,969 B2 | 6/2010 | Bleich | |
| 7,794,448 B2 | 9/2010 | Grandt | |
| 7,798,999 B2 | 9/2010 | Bailey | |
| 8,112,159 B2 | 2/2012 | Harris et al. | |
| 8,206,370 B2 | 6/2012 | von Oepen | |
| 8,298,210 B2 | 10/2012 | Provost-Tine | |
| 8,313,496 B2 | 11/2012 | Sauer | |
| 8,348,899 B2 | 1/2013 | Chesnin | |
| 8,585,950 B2 | 11/2013 | Appling | |
| 8,974,486 B2 | 3/2015 | Kotler | |
| 9,089,258 B2 | 7/2015 | Goldfarb | |
| 9,149,602 B2 | 10/2015 | Chow | |
| 9,265,407 B2 | 2/2016 | Goldfarb | |
| 9,468,362 B2 | 10/2016 | Goldfarb | |
| 9,604,050 B2 | 3/2017 | Barker | |
| 2001/0044591 A1 * | 11/2001 | Stevens | A61M 25/0147 |
| | | | 604/6.14 |
| 2002/0007144 A1 * | 1/2002 | Snoke | A61M 25/0136 |
| | | | 604/95.04 |
| 2002/0062143 A1 * | 5/2002 | Baudino | A61N 1/36071 |
| | | | 607/116 |
| 2003/0028146 A1 * | 2/2003 | Aves | A61B 17/3401 |
| | | | 604/272 |
| 2003/0163082 A1 | 8/2003 | Mertens | |
| 2004/0092863 A1 | 5/2004 | Raulerson | |
| 2004/0116848 A1 * | 6/2004 | Gardeski | A61M 25/0152 |
| | | | 604/95.01 |
| 2005/0004555 A1 * | 1/2005 | Pursley | A61M 25/0152 |
| | | | 604/528 |
| 2005/0059925 A1 | 3/2005 | Maginot | |
| 2005/0096585 A1 | 5/2005 | Schon | |
| 2005/0228339 A1 | 10/2005 | Clark | |
| 2005/0283111 A1 | 12/2005 | Maurice | |
| 2006/0122458 A1 | 6/2006 | Bleich | |
| 2006/0247751 A1 * | 11/2006 | Seifert | A61N 1/057 |
| | | | 607/122 |
| 2007/0006697 A1 | 3/2007 | Assell | |
| 2007/0225661 A1 | 9/2007 | Ash | |
| 2007/0244430 A1 * | 10/2007 | Bedell | A61M 25/0662 |
| | | | 604/93.01 |
| 2007/0249896 A1 | 10/2007 | Goldfarb | |
| 2008/0065049 A1 * | 3/2008 | Harris | A61M 25/0152 |
| | | | 604/525 |
| 2008/0082079 A1 | 4/2008 | Braga | |
| 2008/0097347 A1 * | 4/2008 | Arvanaghi | A61B 10/0233 |
| | | | 604/264 |
| 2009/0192435 A1 | 7/2009 | Gregersen | |
| 2009/0204052 A1 | 8/2009 | Nimkar | |
| 2009/0204079 A1 | 8/2009 | Nimkar | |
| 2009/0205189 A1 | 8/2009 | Nimkar | |
| 2009/0209940 A1 | 8/2009 | Nimkar | |
| 2009/0281379 A1 | 11/2009 | Binmoeller | |
| 2010/0249726 A1 | 9/2010 | Al-Rasheed | |
| 2011/0202067 A1 * | 8/2011 | Falkner | A61M 25/0026 |
| | | | 606/129 |
| 2014/0018772 A1 | 1/2014 | Ash | |
| 2017/0143890 A1 | 5/2017 | Nardeo | |

* cited by examiner

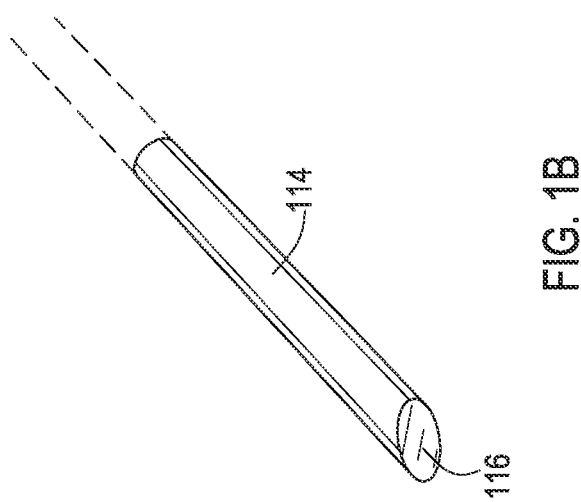

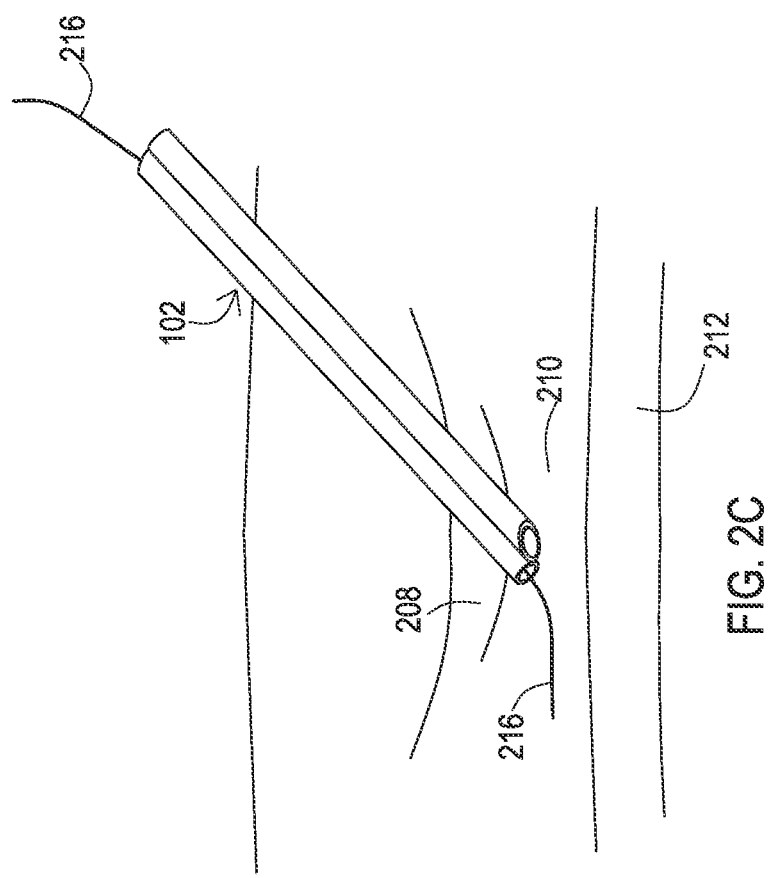

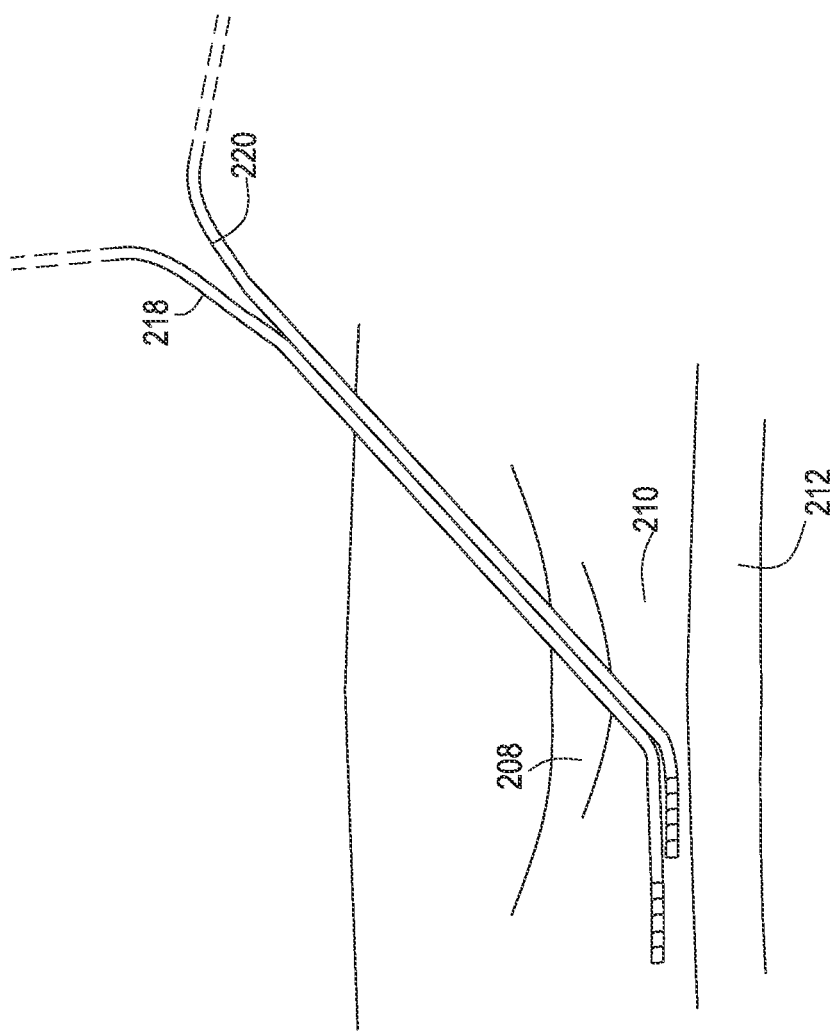

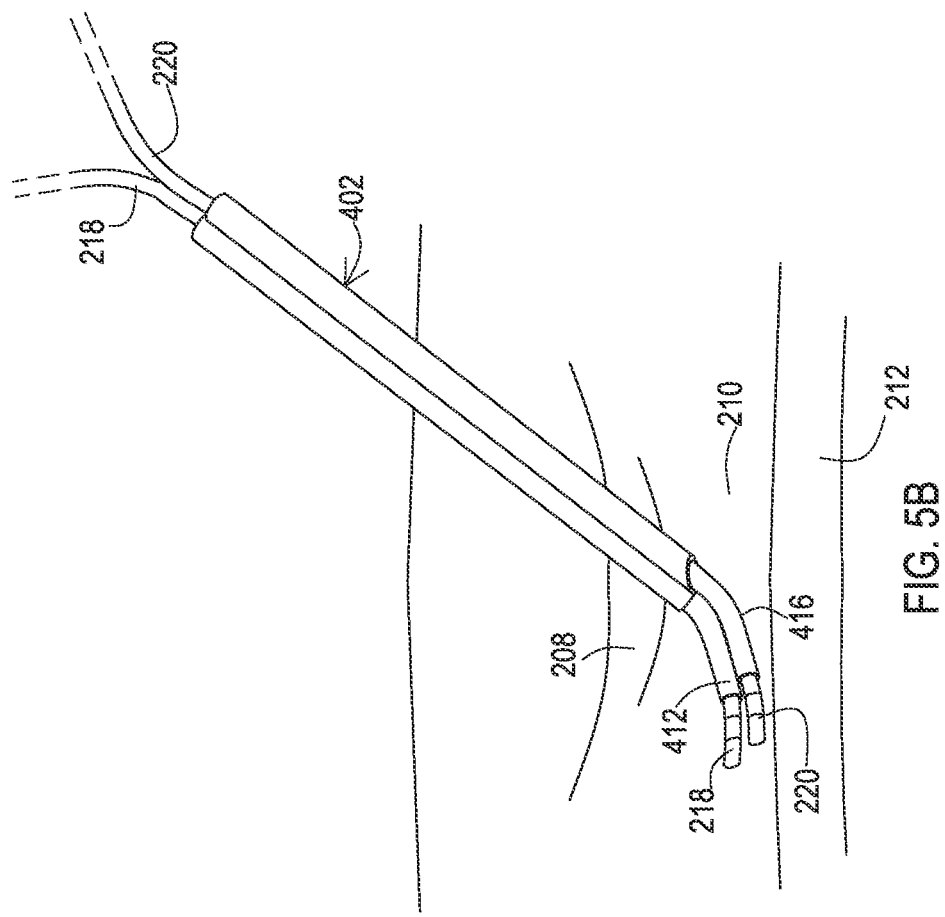

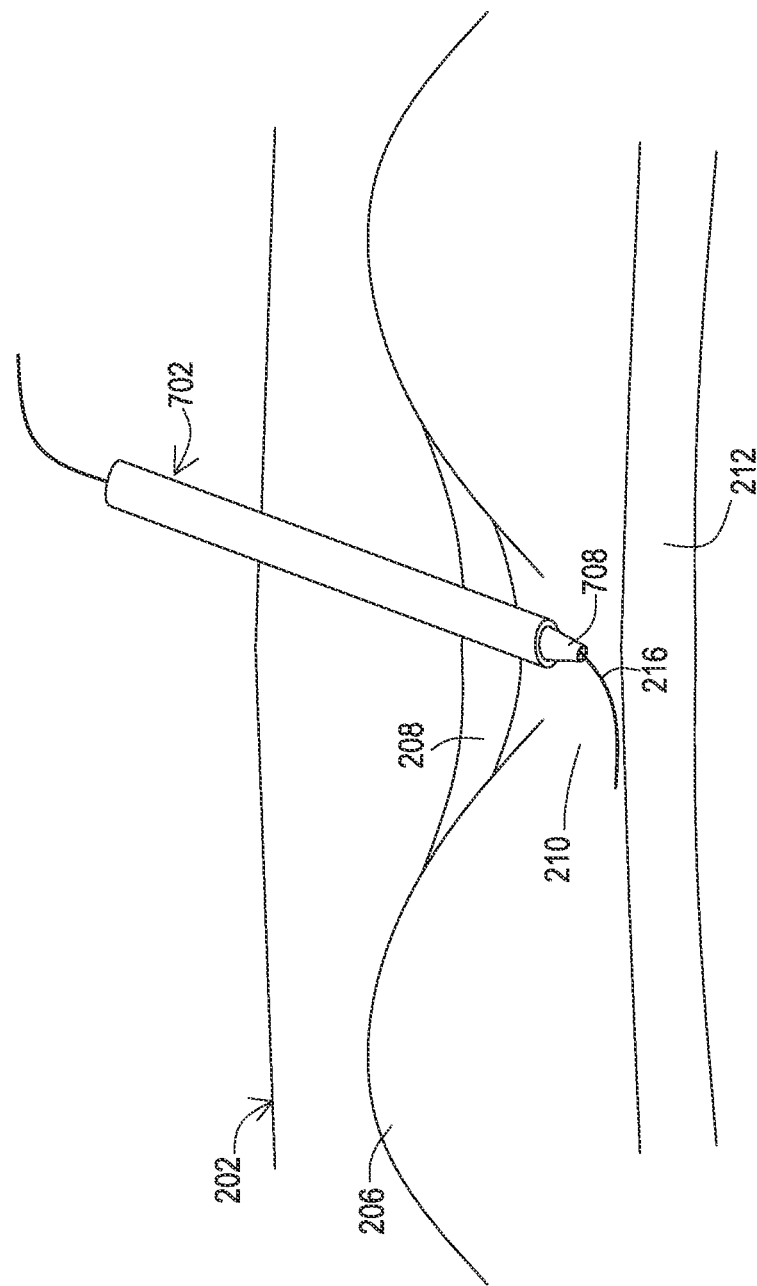

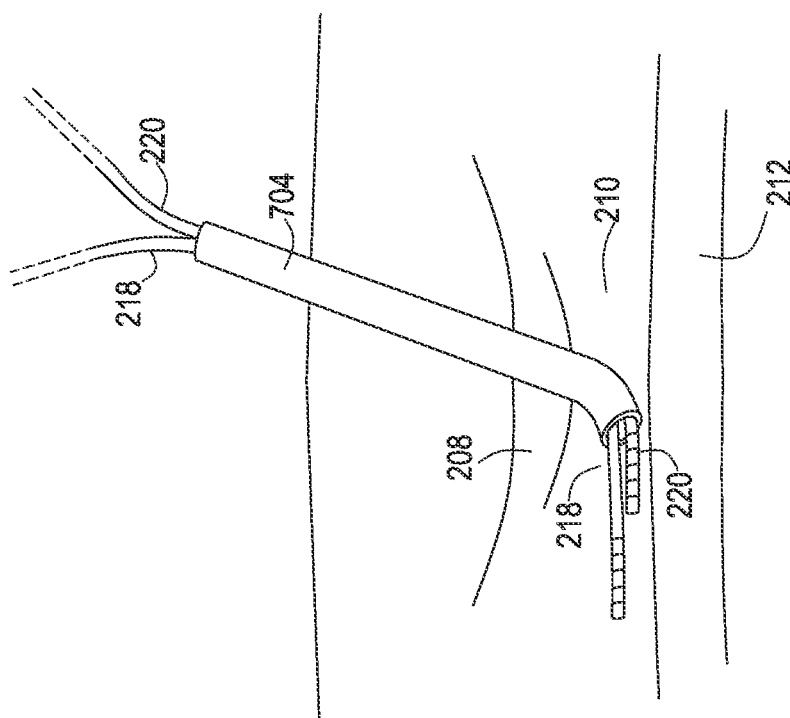

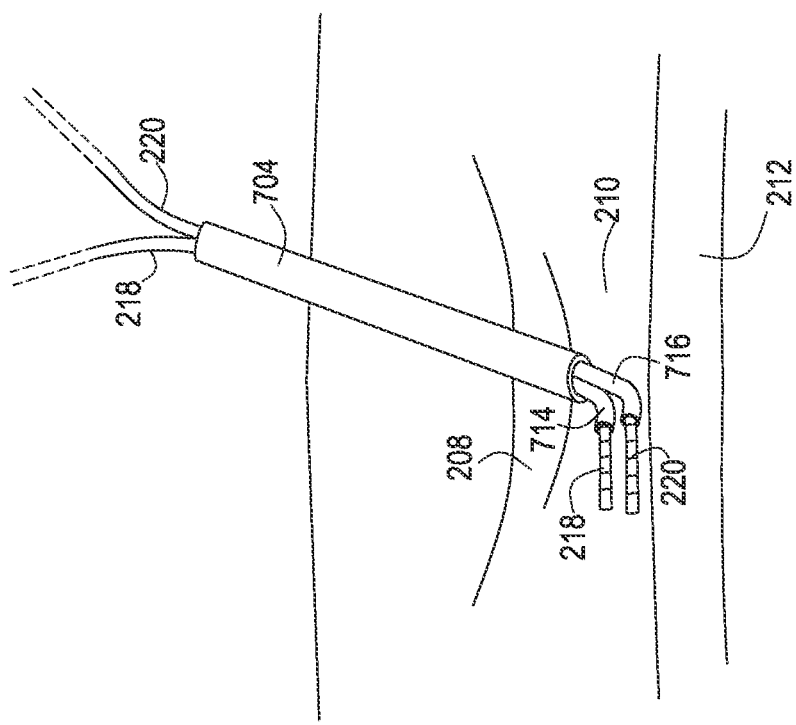

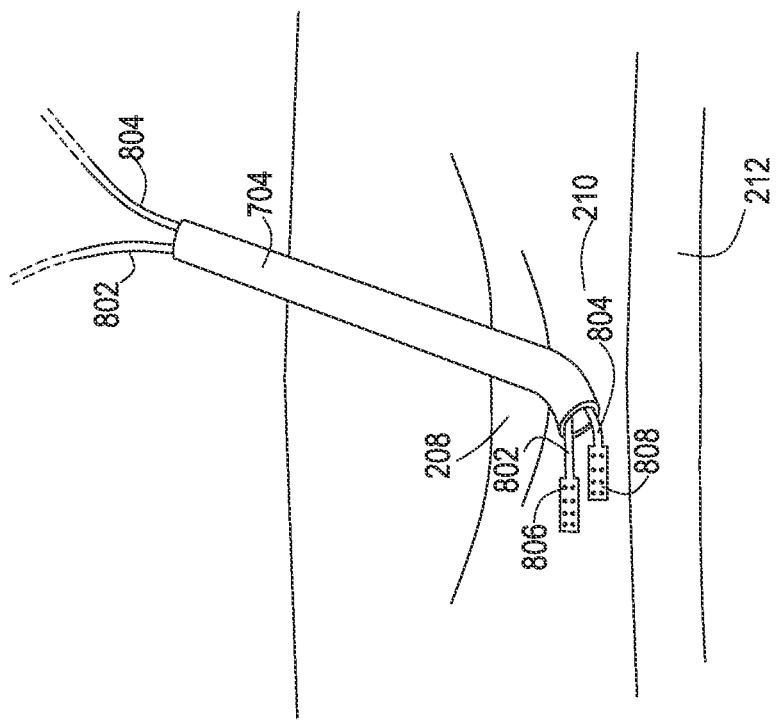

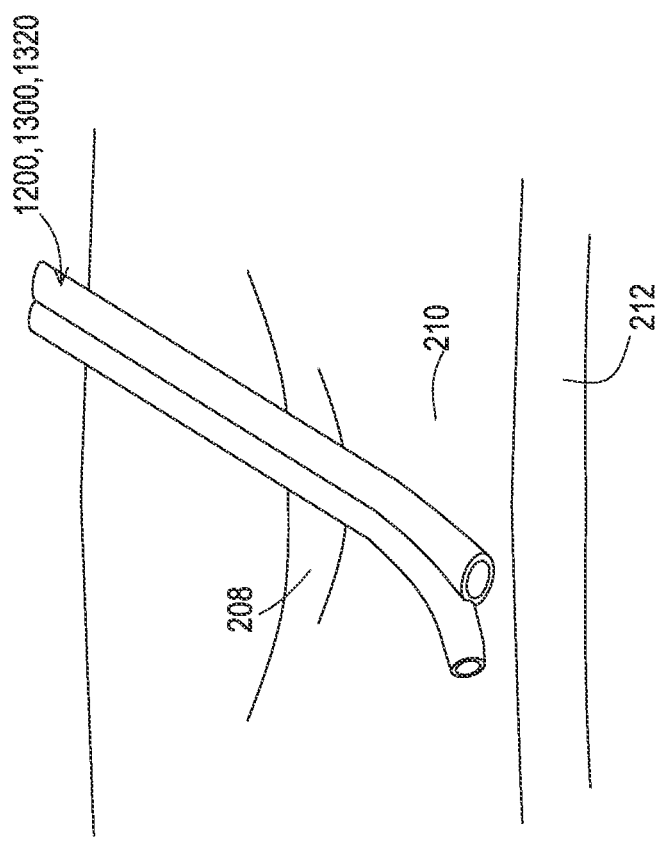

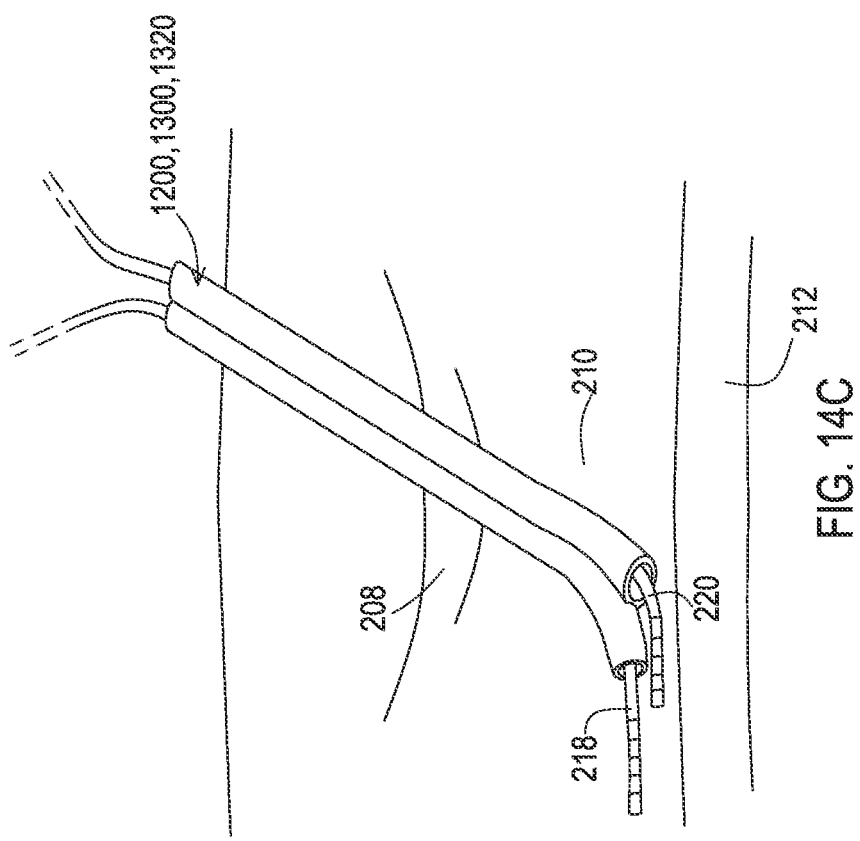

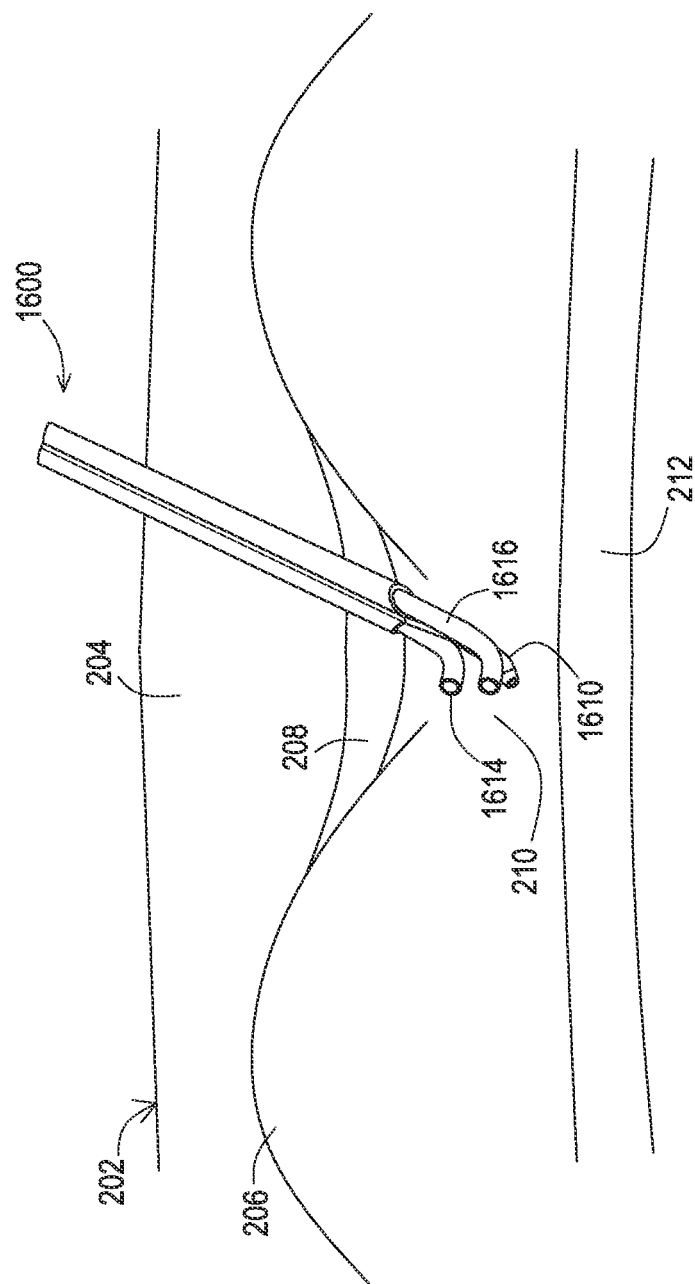

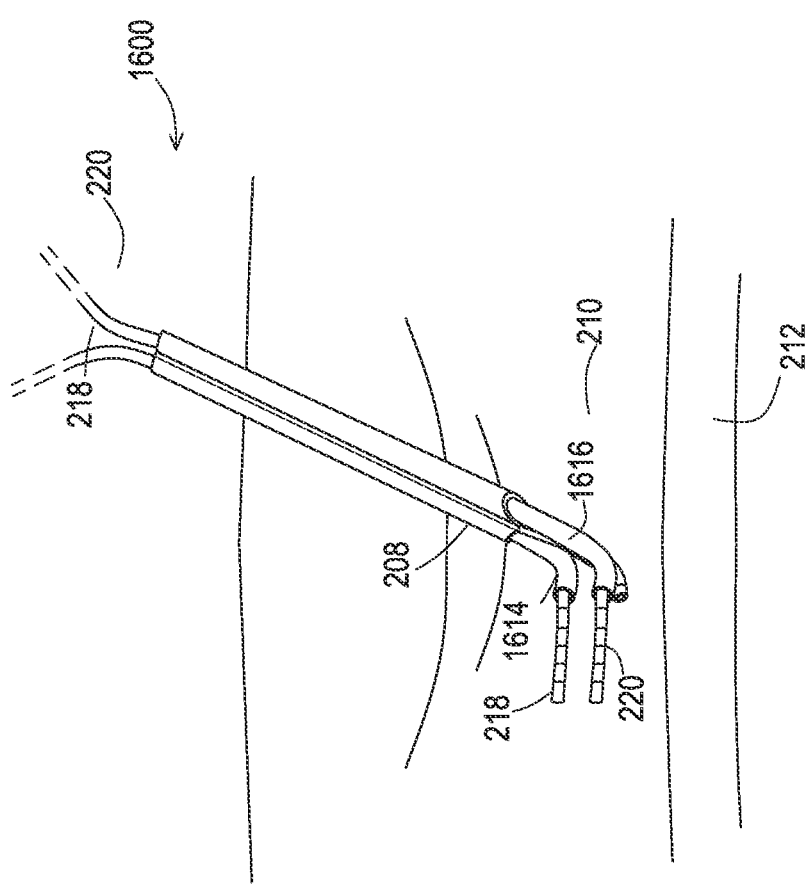

MEDICAL ASSEMBLIES AND METHODS FOR IMPLANTATION OF MULTIPLE MEDICAL LEADS THROUGH A SINGLE ENTRY

CROSS-REFERENCE TO RELATED APPLICATIONS

The present application is a continuation of U.S. patent application Ser. No. 13/525,560, filed Jun. 18, 2012, entitled "MEDICAL ASSEMBLIES AND METHODS FOR IMPLANTATION OF MULTIPLE MEDICAL LEADS THROUGH A SINGLE ENTRY" now U.S. Pat. No. 10,758, 262, which claims priority to U.S. Provisional Patent Application No. 61/498,906, filed Jun. 20, 2011, entitled "Medical Assemblies and Methods for Implementation of Multiple Medical Leads Through a Single Entry"; and U.S. Provisional Patent Application No. 61/498,914, filed Jun. 20, 2011, entitled "Medical Assemblies and Methods for Implementation of Multiple Medical Leads Through a Single Entry", and all the aforementioned applications are incorporated by reference herein as if each is re-written in its entirety.

Provisional Patent Application No. 61/498,914, filed Jun. 20, 2011, entitled "Medical Assemblies and Methods for Implementation of Multiple Medical Leads Through a Single Entry", and both applications are incorporated by reference herein as if each is re-written in its entirety.

TECHNICAL FIELD

Embodiments are related to medical assemblies for implantation of medical leads into a body. More particularly, embodiments are related to medical assemblies for implantation of multiple medical leads through a single entry to a defined space within the body.

BACKGROUND

Medical leads are implanted into a defined space within a body of a patient to provide medical therapy within the defined space. For instance, a distal end of one or more medical leads may be implanted within an epidural space of the patient in order to deliver electrical stimulation pulses from electrodes on the distal end of the lead(s). The electrical stimulation may be for various reasons, for instance, to provide pain management.

In situations where multiple leads are needed, the conventional manner of implantation is to perform two separate implantation procedures, with each procedure creating a separate entry to the defined space. In the example of the epidural space, each lead must pass through the ligamentum flavum in order to enter the epidural space. The conventional implantation process involves puncturing the ligamentum flavum with a needle large enough to pass a first medical lead through a lumen of the needle. A needle is then used to again puncture the ligamentum flavum at a different site to allow a second medical lead to pass through the needle and into the epidural space.

Each time an entry is created for each lead, there may be additional patient discomfort and inconvenience. Furthermore, there is also an increased risk of complications such as an infection or other adverse condition. For instance, in the case of puncturing the ligamentum flavum to reach an epidural stimulation site, each puncture creates a risk of also puncturing the dura and causing a cerebral spinal fluid leak.

SUMMARY

Embodiments address issues such as these and others by providing assemblies that allow for implantation of multiple leads through a single entry. In this manner, the risks and inconveniences of implanting multiple leads may be reduced. For example, the assemblies may include features such as catheters with multiple lumens, catheters with multiple sheaths, and/or catheters with a lumen having an oblong lateral cross-section. The leads may be implanted by being inserted through the lumens and/or sheaths of the catheters, where the catheter and/or sheaths may be deflectable so to facilitate directing the lead within the defined space of the body.

Embodiments provide a medical assembly that includes a catheter having multiple lumens and a deflectable distal end. A trocar is disposed within a first of the lumens, and a guide wire is disposed within a second of the lumens.

Embodiments provide a medical assembly that includes a catheter having multiple lumens. A first sheath is disposed within a first of the lumens, the first sheath being deflectable. A second sheath is disposed within a second of the lumens, the second sheath being deflectable.

Embodiments provide a medical assembly that includes a catheter having a lumen with an oblong lateral cross-section. A first sheath is disposed within the lumen, the first sheath being deflectable. A second sheath is disposed within the lumens, the second sheath being deflectable.

Embodiments provide a medical assembly that includes a catheter having a lumen with an oblong lateral cross-section and having a distal end with a pre-formed bend. An introducer is present within the lumen of the catheter, and the introducer is positioned within the lumen at the distal end of the catheter such that the pre-formed bend is held straight.

Embodiments provide a method of inserting a medical assembly. The method involves inserting a needle into a defined space within a patient and feeding a guide wire through a lumen of the needle to position the guide wire into the defined space. The method further involves removing the needle while maintaining the guide wire within the defined space and feeding a catheter with multiple lumens along the guide wire by passing the guide wire through one of the multiple lumens. Additionally, the method involves deflecting a distal end of the catheter when the catheter enters the defined space.

Embodiments provide a method of inserting a medical assembly. The method involves inserting a needle into a defined space within a body and feeding a guide wire through a lumen of the needle to position the guide wire into the defined space. The method further involves removing the needle while maintaining the guide wire within the defined space and feeding a catheter with multiple lumens along the guide wire by passing the guide wire through one of the multiple lumens. Additionally, the method involves forcing a first sheath within one of the lumens of the catheter into the defined space where the first sheath then deflects.

Embodiments provide a method of inserting a medical assembly. The method involves providing a catheter with a lumen having an oblong lateral cross section, the catheter having an introducer present within the lumen, the introducer having a lumen, the catheter having a distal end with a pre-formed bend that is straightened by the presence of the introducer within the lumen of the catheter at the distal end. The method further involves feeding the catheter within the introducer present within the lumen of the catheter along a guide wire by passing the guide wire through the lumen of the introducer until the distal end enters a predefined space within a body. The method further involves removing the introducer to allow the distal end of the catheter to achieve the pre-formed bend within the defined space and inserting a first medical lead and a second medical lead through the lumen of the catheter with a distal end of the first medical lead and the second medical lead entering the defined space.

Embodiments provide a medical assembly that includes a catheter having multiple lumens and a deflectable distal end and a trocar disposed within a first of the multiple lumens. The medical assembly further includes a needle disposed within a second of the lumens with a distal tip of the needle being exposed from the second of the lumens.

Embodiments provide a method of inserting a medical assembly that involves inserting a needle into a defined space within a patient, the needle being present within one lumen of a catheter having multiple lumens with a distal tip of the needle being exposed from the one lumen. The method further involves upon the needle and catheter entering the defined space, retracting the needle within the one lumen and deflecting a distal end of the catheter within the defined space.

Embodiments provide a medical assembly that includes a catheter having multiple lumens and a deflectable distal end. The medical assembly further includes a first sheath disposed within a first of the multiple lumens and a needle disposed within a second of the lumens with a distal tip of the needle being exposed from the second of the lumens.

Embodiments provide a method of inserting a medical assembly that involves inserting a needle and a catheter into a defined space within a patient, the needle being present within one lumen of the catheter having multiple lumens with a distal tip of the needle being exposed from the one lumen. The method further involves upon the needle and catheter entering the defined space, removing the needle from the one lumen and forcing a first sheath within one of the lumens of the catheter into the defined space where the first sheath then deflects.

Embodiments provide a medical assembly that includes a catheter having a lumen with an oblong lateral cross-section and an introducer present within the lumen of the catheter, the introducer having a lumen. A needle is present within the lumen of the introducer with a distal tip of the needle being exposed beyond a distal end of the introducer and the catheter.

Embodiments provide a method of inserting a medical assembly that involves providing a catheter with a lumen having an oblong lateral cross section, the catheter having an introducer present within the lumen, the introducer having a lumen with a needle present within the lumen of the introducer with a distal tip of the needle exposed beyond a distal end of the introducer and catheter. The method further involves inserting the needle into a body until the distal end of the needle and the catheter enters a predefined space within the body and removing the needle and the introducer. The method further involves inserting a first medical lead and a second medical lead through the lumen of the catheter with a distal end of the first medical lead and the second medical lead entering the defined space.

DESCRIPTION OF THE DRAWINGS

FIG. 1B shows one example of a trocar that may be used with the assembly of FIG. 1A.

FIGS. 2A-2E show the assembly of FIG. 1A during an implantation procedure.

FIGS. 5A-5B show the assembly of FIG. 4 during an implantation procedure.

FIGS. 8A-8B show the assembly of FIG. 7A during one implantation procedure.

FIGS. 14A-14C show the assembly of FIG. 12 during an implantation procedure.

FIGS. 17A-17B show the assembly of FIG. 16 during an implantation procedure.

DETAILED DESCRIPTION

Embodiments provide assemblies for implanting multiple medical leads through a single entry to a defined space within the body, such as the epidural space. The assemblies include a catheter that may have features such as multiple lumens, an extended lumen adjacent other lumens, multiple sheaths within one or more of the multiple lumens, and/or a lumen having an oblong lateral cross-section. The various embodiments may utilize one or more of implantation needles, guidewires, and the like to introduce the catheter into the defined space through the single entry.

Figure 1A:
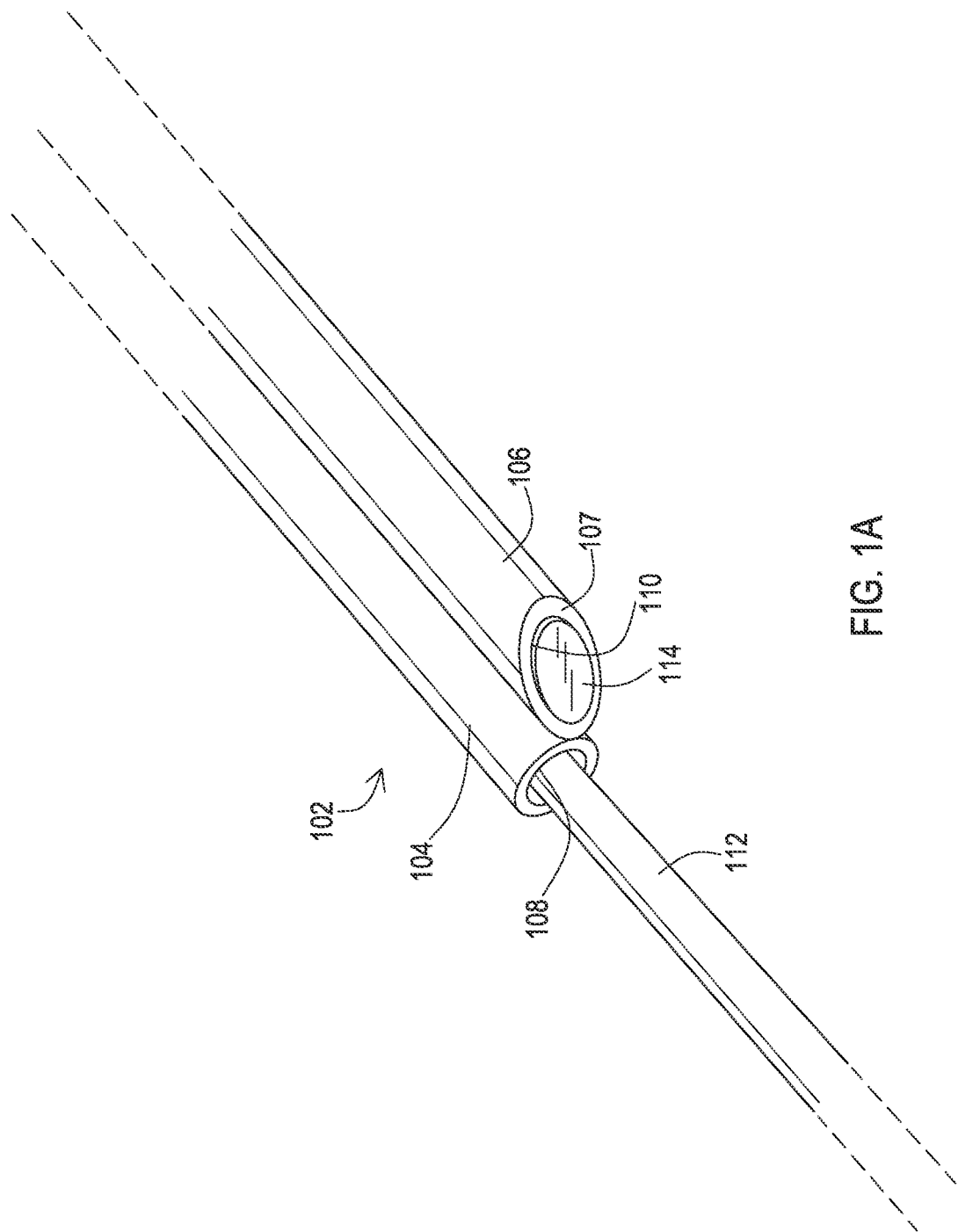
FIG. 1A shows a first example of an assembly for implanting multiple medical leads through a single entry by way of a catheter with multiple lumens and a deflectable distal end.

FIG. 1A shows one example of a medical assembly for implanting multiple medical leads into a defined space within a body. The assembly includes a multi-lumen catheter 102 that may be implanted into the defined space to provide a passageway for the multiple leads to then be inserted. The catheter 102 includes a first lumen body 104 and a second lumen body 106 that are integrally formed and may be a unitary structure, each defining a respective lumen 108, 110. In this example, the lumen body 104 is used as a guide that follows along a guidewire 112 passing through the lumen 108 where the guidewire 112 has already been inserted into the defined space.

In this particular example, the catheter 102 has a deflectable distal end shown in FIG. 1A. This allows the distal end to deflect upon entering the defined space so as to avoid damaging the tissues surrounding the defined space and so as to properly direct the leads once they are inserted. The deflectability may be achieved by having the catheter be constructed of flexible materials. For instance, the catheter may be constructed of nylon or similar materials, may have an internal liner also constructed of nylon, and may also include an internal reinforcement such as a braid constructed of a metal such as stainless steel. Furthermore, the deflectable end may be constructed of shape memory materials such as Nylon, Polyurethane, or any other thermoplastics, thermoplastic elastomers, and the like. The desired bend of the distal end may be pre-formed through a heat forming process, and then held straight by a trocar so that once the trocar is removed, the distal end achieves the bent configuration.

However, there may be a need for the distal end to be relatively stiff in order to penetrate through tissue that is present in the pathway to the defined space. For instance, the defined space may be the epidural space where access is achieved by piercing through the ligamentum flavum that requires a relatively stiff catheter 102 even where a needle has previously been inserted, especially when the needle is of a smaller diameter than the multi-lumen catheter 102. Yet, the epidural space is bordered by the spinal cord such that care must be exercised when attempting to insert objects such as catheters and leads into the epidural space.

Figure 1C:
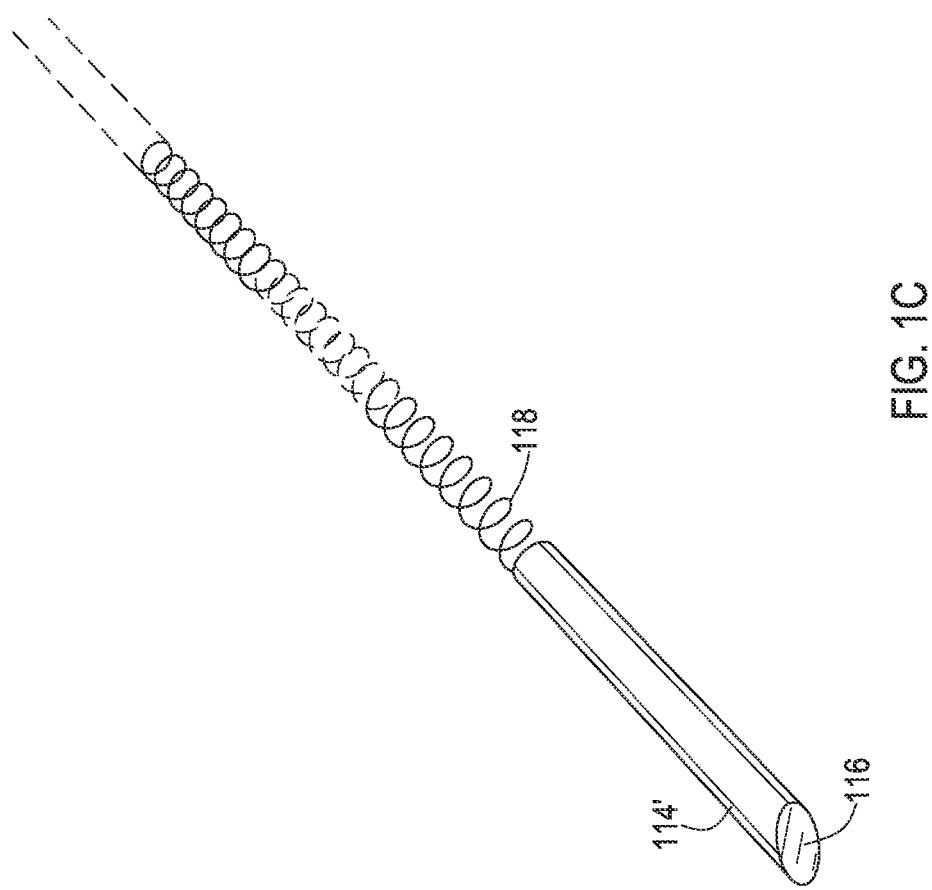
FIG. 1C shows another example of a trocar that may be used with the assembly of FIG. 1A.

To avoid damaging contact with the spinal cord, the catheter 102 has the deflectable distal end such that upon entering the epidural space, the catheter tip deflects as discussed above to an orientation largely parallel to the spinal cord such as by following the guidewire 112 and/or by using shape memory. However, to pierce the ligamentum flavum, the catheter 102 must have a rigid distal tip. To achieve this initially rigid but later deflectable configuration, a trocar 114 made of a rigid material such as a hard plastic or metal is present within the lumen 110 which creates a rigid distal tip and which holds the catheter in a straight configuration during insertion. The trocar 114 may be retractable, such as where the trocar 114 is solid as shown in FIG. 1B such that the trocar 114 is retracted proximally once the ligamentum flavum is pierced to allow the distal tip of the catheter 102 to then deflect such as by transitioning to a pre-formed bend. Alternatively, such as where the catheter relies upon the guidewire to control deflection rather than shape memory, the trocar 114' as shown in FIG. 1C may include a flexible region 118 such as a coiled area that can deflect and thereby allow the catheter 102 to deflect with the trocar 114' in place.

To also assist in piercing the tissue such as the ligamentum flavum, the lumen body 106 of the catheter 102 may include a beveled distal end 107. Likewise, the trocar 114, 114' may include a beveled distal end 116 which may be oriented with the bevel in the same plane as the bevel of the lumen body 106 as shown in FIG. 1A.

FIGS. 2A-2E show a series of phases of the multi-lumen catheter 102 being inserted and the implantable medical leads ultimately being inserted into the defined space. These phases are illustrated and discussed with reference to implantation into the epidural space of a body. However, it will be appreciated that the assemblies and techniques may also be applicable to other defined spaces within a body. FIG. 3 shows a series of acts taken to progress through the phases of FIGS. 2A-2E. Additionally, while a hub is not shown on a proximal end of the needle and catheter, it will be appreciated that a hub may be present for each device to allow insertion and removal of the various objects.

Figure 2A:
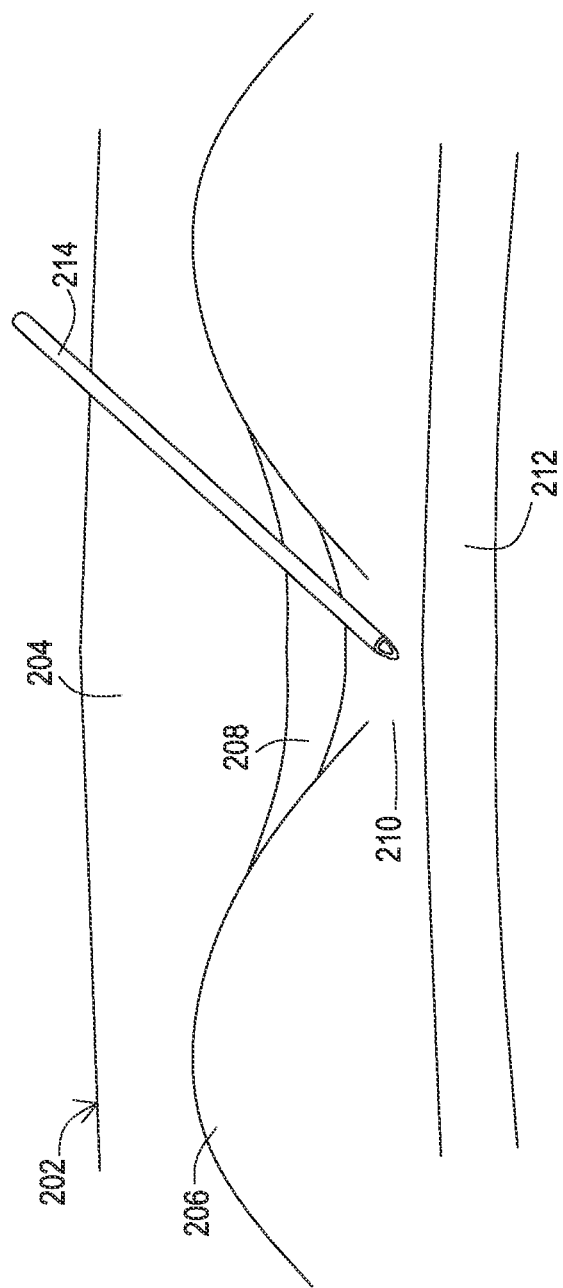
Figure 2B:
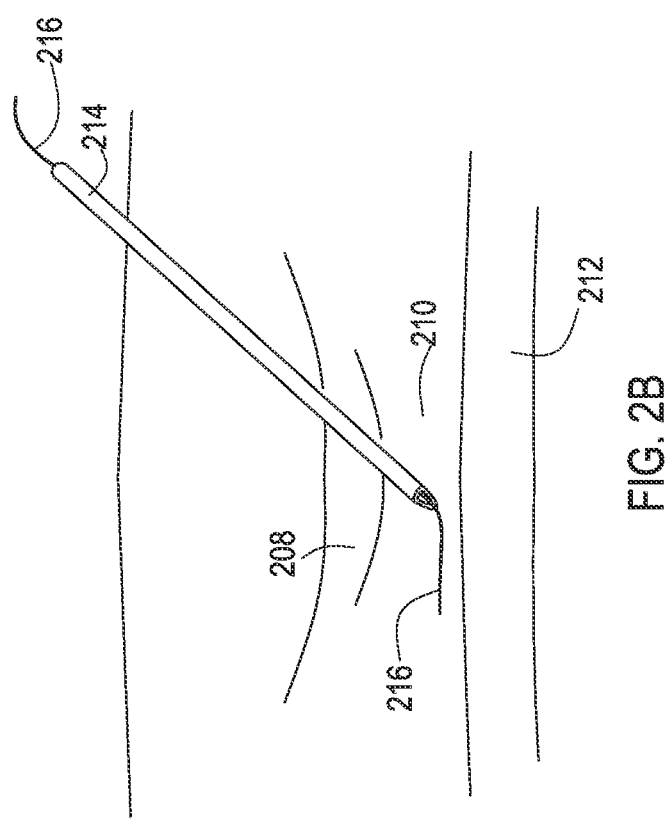
Figure 3:
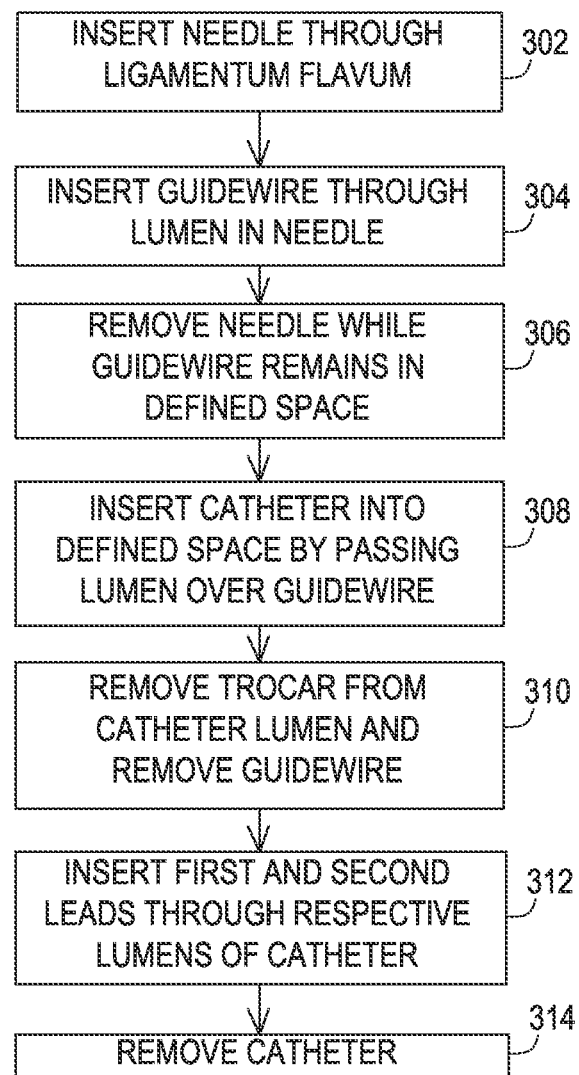
FIG. 3 shows a set of acts that utilize the assembly of FIG. 1A to implant multiple medical leads.

FIG. 2A shows a needle 214 being inserted into a body 202 by passing through the skin 204 and through the ligamentum flavum 208, adjacent vertebral bones 206 pursuant to the needle operation 302 of FIG. 3. The needle 214 enters the epidural space 210 but care is exercised to avoid contact with the dura or any other layers about the spinal cord 212. FIG. 2B shows a guidewire 216 being inserted into the epidural space 210 by feeding the guidewire 216 through a lumen within the needle 214 pursuant to the guidewire operation 304 of FIG. 3. The needle 214 is then removed while maintaining the guidewire in position within the epidural space pursuant to a needle operation 306.

FIG. 2C shows the catheter 102 then being inserted into the epidural space 210 by feeding the catheter 102 along the guidewire 216 with the guidewire 216 passing through the lumen 108 of the lumen body 104 pursuant to a catheter operation 308. The trocar 114 is then removed from the catheter 102 in this example where the trocar 114 as shown in FIG. 1B is solid pursuant to a removal operation 310 which allows the catheter 102 to be inserted farther such that the distal tip deflects as it follows the path of the guidewire 216 and/or deflects by achieving a pre-formed bend. Where the trocar 114' as shown in FIG. 1B_is present and includes a flexible portion 118 also shown in FIG. 1B, the trocar 114' of FIG. 1B may remain in place as the distal end begins to deflect and then is removed once the catheter 102 is inserted to an approximate final position within the epidural space. In either case, once the catheter 102 is inserted to the approximate final position, the guidewire 216 is then removed pursuant to the removal operation 310.

Figure 2D:
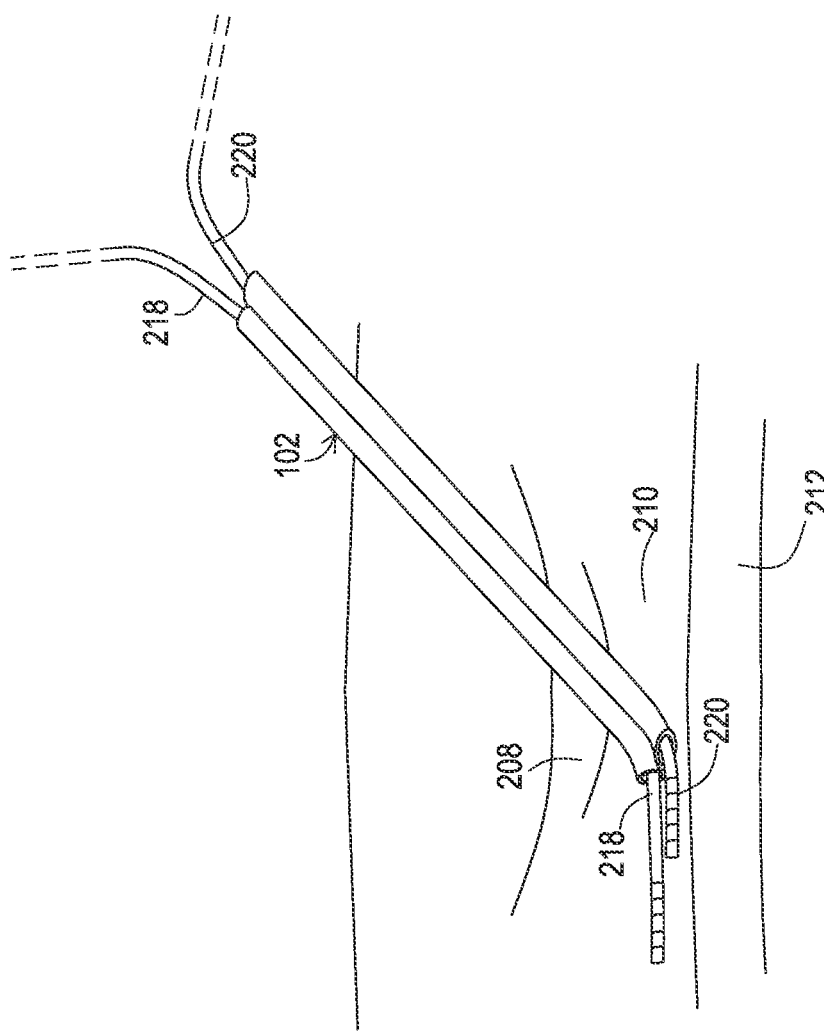

FIG. 2D then shows first and second implantable medical leads 218, 220 being inserted through each lumen of the catheter 102 so that the medical leads 218, 220 are then directed into the epidural space and in a direction largely parallel to the spinal cord 212 and pursuant to an insertion operation 312. Once the medical leads 218, 220 have reached an approximate final position within the epidural space 210, the catheter 102 is then removed pursuant to a removal operation 314 to leave the medical leads 218, 220 in position within the epidural space 210 as shown in FIG. 2E.

Figure 4:
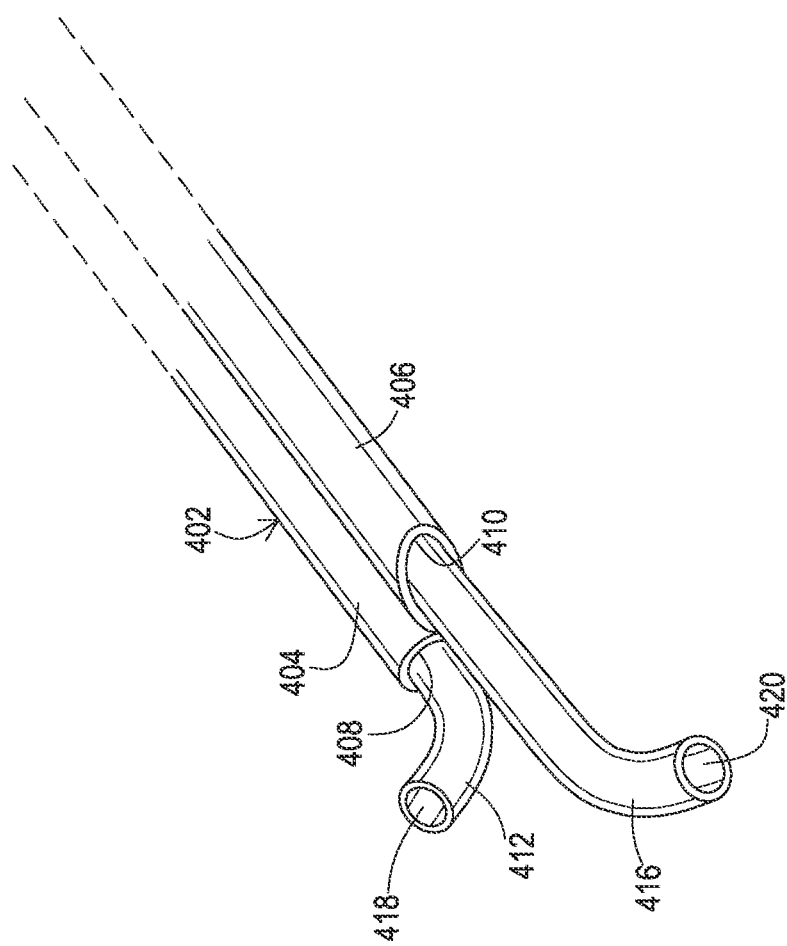
FIG. 4 shows a second example of an assembly for implanting multiple medical leads through a single entry by way of a catheter with multiple lumens, each lumen containing a deflectable sheath.

FIG. 4 shows another example of a medical assembly for implanting multiple medical leads into a defined space within a body. The assembly includes a multi-lumen catheter 402 that may be implanted into the defined space to provide a passageway for the multiple leads to then be inserted. The catheter 402 includes a first lumen body 404 and a second lumen body 406 that are integrally formed and may be a unitary structure, each defining a respective lumen 408, 410. In this example, the lumen body 404 may also be used as a guide that follows along a guidewire passing through the lumen 108 where the guidewire has already been inserted into the defined space.

In this particular example, the catheter 402 has first and second deflectable sheaths 412, 416 that are present within the multiple lumens 408, 410, respectively. This allows the distal end of the sheaths to deflect upon the catheter 402 entering the defined space so as to avoid damaging the tissues surrounding the defined space and so as to properly direct the leads once they are inserted through lumens 418, 420 within the sheaths 412, 416. The sheaths 412, 416 may be deflectable by constructing them from a flexible material. For instance, the sheaths may be constructed of various layers and materials such as nylon, may have an internal liner also constructed of various materials such as high density polyethylene and the like, and may also include an internal reinforcement such as a braid constructed of a metal such as stainless steel. The sheaths 412, 416 may also utilize shape memory to establish pre-formed bends on the distal ends where the preformed bends are held straight by the catheter 402 and are achieved upon the distal ends of the sheaths 412, 416 exiting the distal end of the catheter 402.

While the distal end of the catheter 402 may be deflectable or may be rigid, there may still be a need for the distal end to be stiffened by a trocar in order to penetrate through tissue that is present in the pathway to the defined space. As with the prior embodiment, the trocar 114 shown in FIG. 1B may be retractable, such as where the trocar 114 is solid as shown in FIG. 1B or may alternatively include a flexible region 118 as shown in FIG. 1C, such as a coiled region, that can deflect and thereby allow the catheter 102 to deflect with the trocar 114' in place as shown in FIG. 1C.

To also assist in piercing the tissue such as the ligamentum flavum, the lumen body 406 of the catheter 402 includes a beveled distal end like the previous embodiment. Likewise, the trocar 114 (as shown in FIG. 1B), 114' (as shown in FIG. 1C) may include a beveled distal end 116 which may be oriented with the bevel in the same plane as the bevel of the lumen body 406 as show in FIG. 4.

Figure 5A:
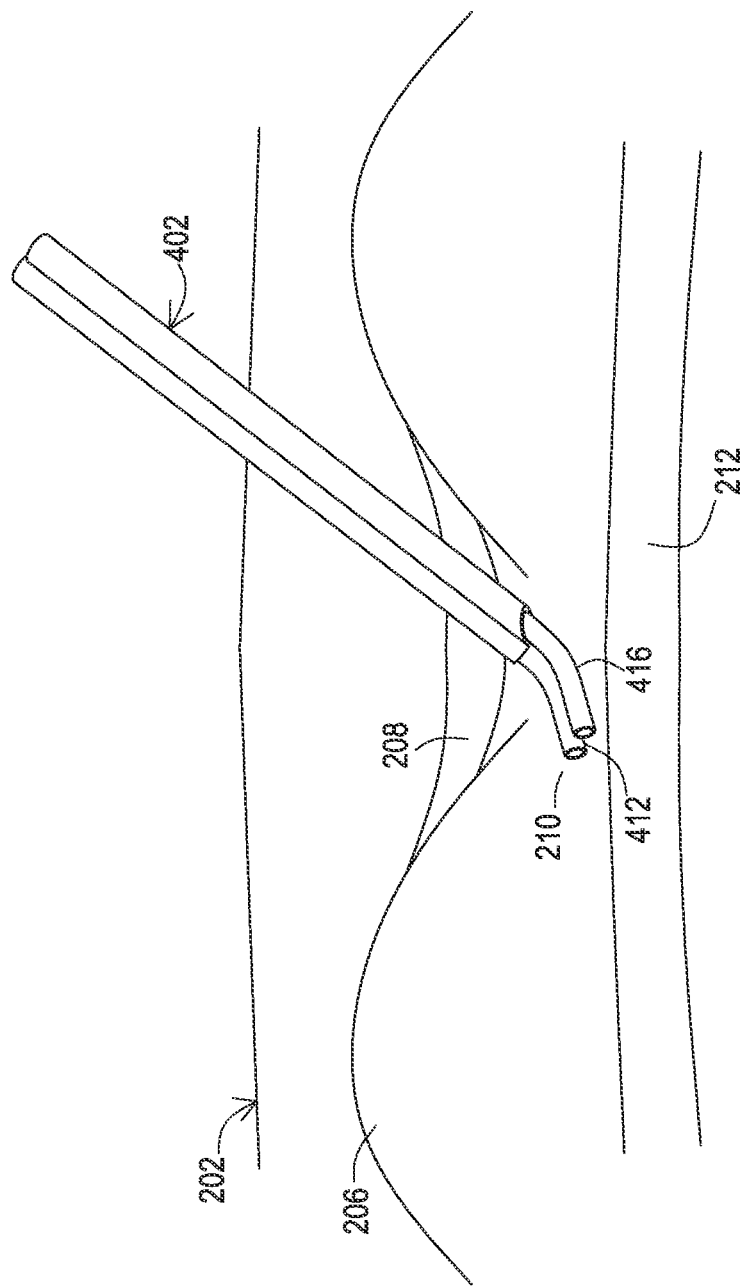
Figure 6:
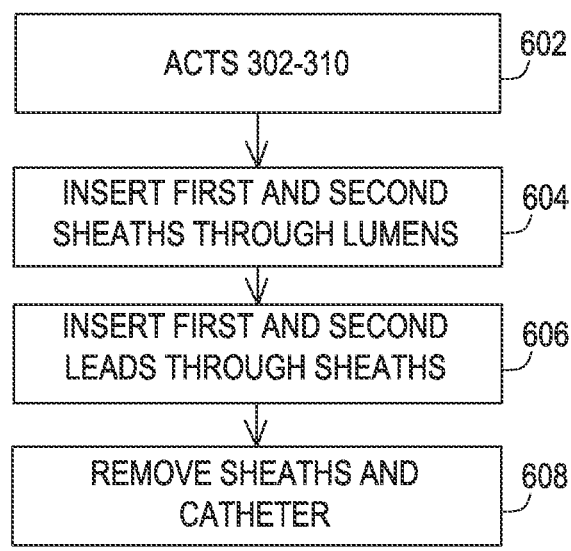
FIG. 6 shows a set of acts that utilize the assembly of FIG. 4 to implant multiple medical leads.

FIGS. 5A-5B show a series of phases of the multi-lumen catheter 402 being inserted and the implantable medical leads ultimately being inserted into the defined space. These phases are also illustrated and discussed with reference to implantation into the epidural space of a body. However, it will be appreciated that the assemblies and techniques may also be applicable to other defined spaces within a body. FIG. 6 shows a series of acts taken to progress through the phases of FIGS. 5A-5B.

Initially, the phases of FIGS. 2A and 2B are performed along with the acts in the operations 302-310 discussed above and pursuant to an initial operation 602. The sheaths 418, 420 may already be present within the catheter lumens 408, 410 when inserting the catheter 402 where in that case the guidewire 216 passes through the sheath lumen 418 while a trocar 114 (as shown in FIG. 1B) may be present within the sheath lumen 420. The guidewire 216 and trocar 114 (as shown in FIG. 1B), if any, are then removed.

Then, as shown in FIG. 5A, the distal ends of the sheaths 412, 416 are extended distally from the catheter 402 pursuant to the sheath operation 604, allowing the distal ends of the sheaths 412, 416 to deflect as needed to obtain an orientation largely parallel to the spinal cord 212. Then, as shown in FIG. 5B, the implantable medical leads 218, 220 are inserted through the sheath lumens 418, 420 to enter into the epidural space 210 and are guided by the sheaths 412, 416 into the orientation that is largely parallel to the spinal cord 212 pursuant to the lead operation 606. The sheaths 412, 416 and catheter 402 may then be removed, individually or as a whole, pursuant to the removal operation 608, which then produces the phase shown in FIG. 2E.

Figure 7A:
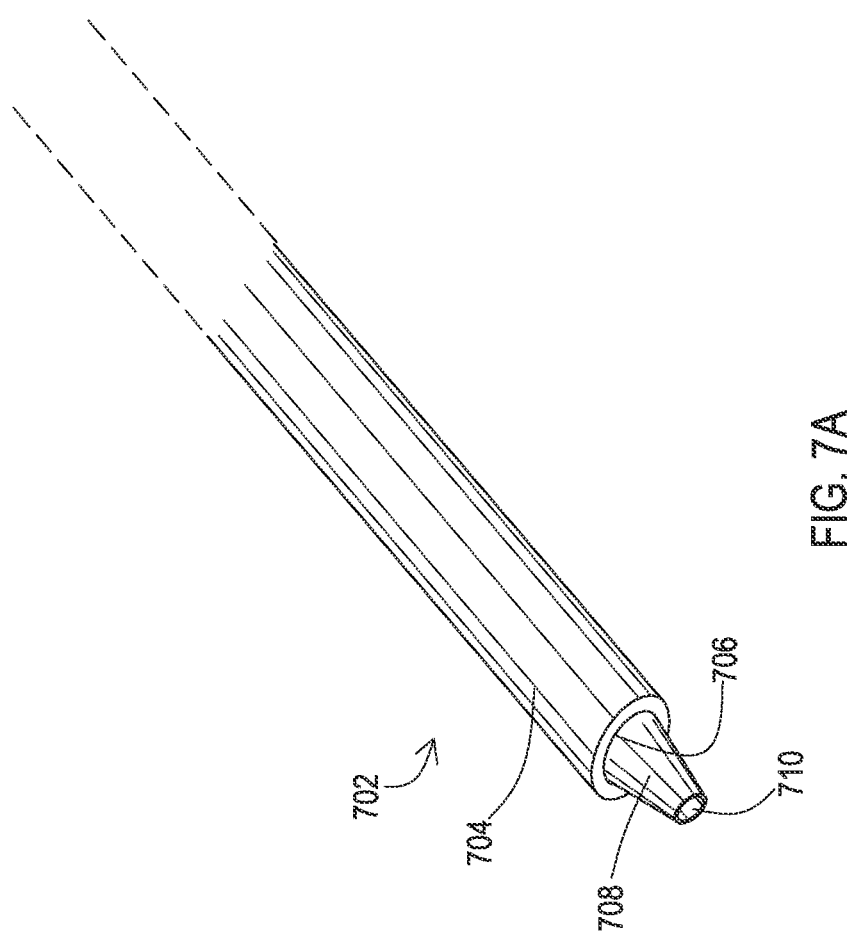
FIG. 7A shows a third example of an assembly for implanting multiple medical leads through a single entry by way of a catheter having a lumen with an oblong lateral cross-section.

FIG. 7A shows another example of a medical assembly for implanting multiple medical leads into a defined space within a body. The assembly includes a catheter 702 having a single lumen body 704 but with a lateral cross-section having an oblong shape such as an ellipse that is capable of receiving multiple medical leads. A removable introducer 708 having a conical distal end for ease of insertion is present within an oblong lumen 706 of the catheter 702 to provide stiffness. The introducer 708 also includes a lumen 710 that may be used to receive a guidewire or a needle during insertion of the catheter 702 into the defined space within the body. The catheter 702 may have a shape memory providing a pre-formed bend on the distal end which is held straight by the introducer 708 and is achieved upon removal of the introducer 708.

Figure 7B:
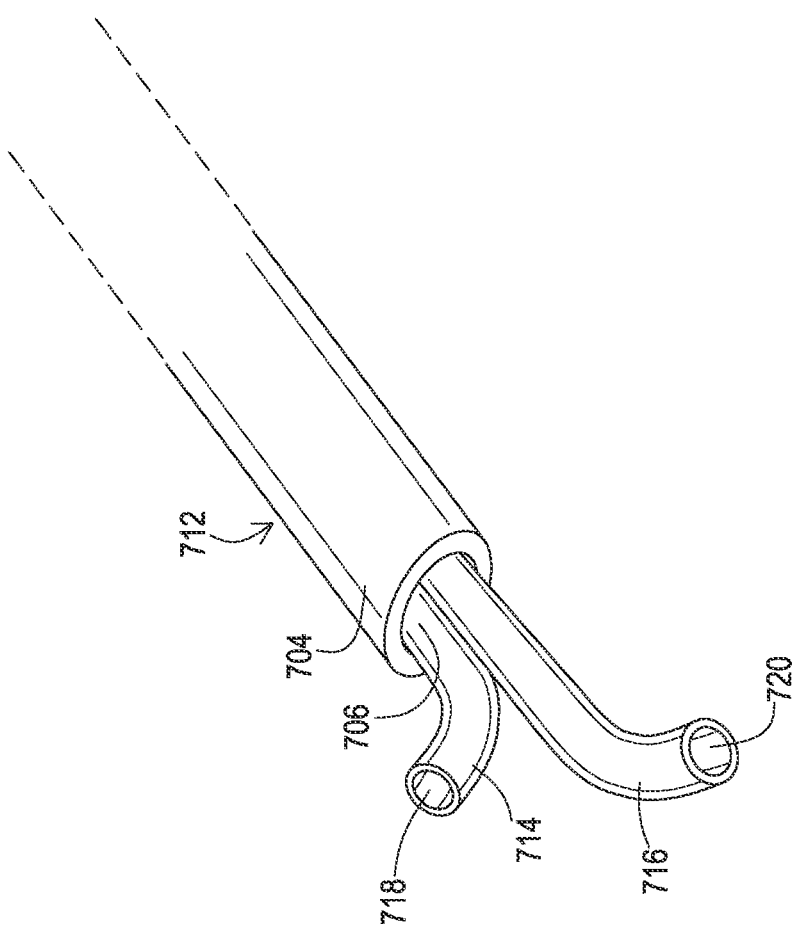
FIG. 7B shows a fourth example of an assembly for implanting multiple medical leads through a single entry by way of a catheter having a lumen with an oblong lateral cross-section and having sheaths within the lumen.

FIG. 7B shows an example of a medical assembly where a catheter 712 has the single lumen body 704 with a lateral cross-section having an oblong shape. In this assembly, sheaths 714 and 716 having sheath lumens 718 and 720 are present within the oblong lumen 706 of the catheter 712. As with sheaths in the embodiment of FIG. 4, these sheaths may be used to ultimately guide the medical leads into place. The sheaths may be deflectable so as to orient in a direction parallel to the spinal cord 212 such as by being constructed of a flexible material and/or by being constructed of a shape memory material to provide pre-formed bends. Such pre-formed bends may be held straight by the catheter 712 and then achieved upon the distal ends being extended from the catheter 712. This catheter 712 may utilize an introducer 708 which is then removed once in the defined space within the body to allow insertion of the sheaths 714, 716.

Figure 8C:
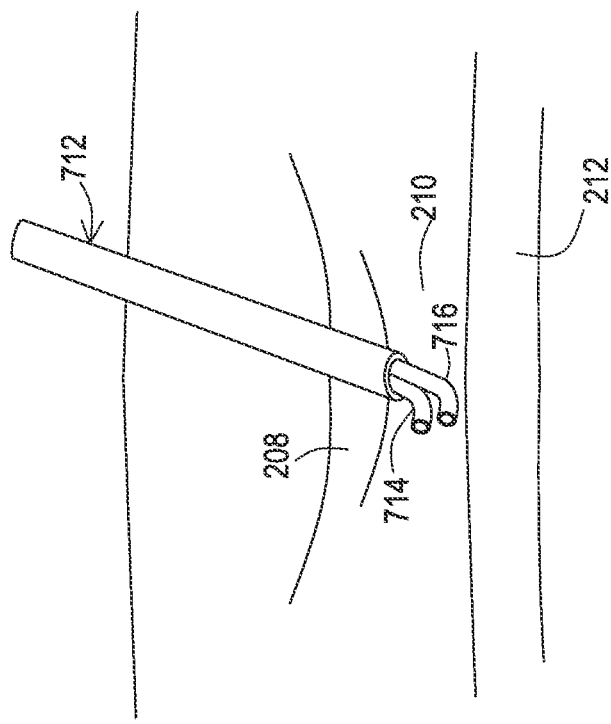
FIGS. 8CA-8CB show the assembly of FIG. 7 during another implantation procedure.
Figure 9A:
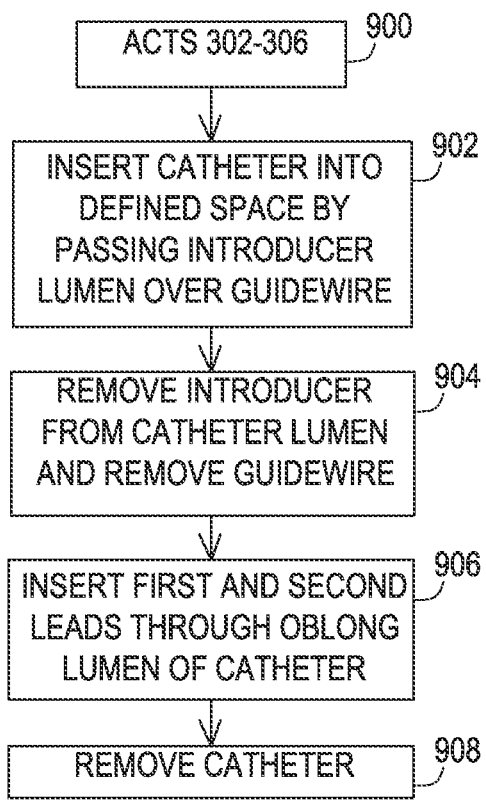
FIG. 9A shows a set of acts that utilize the assembly of FIG. 7A to implant multiple medical leads.

FIG. 8A shows an assembly including catheter 702 being inserted into the epidural space 210 in accordance with guidewire operation 902 of FIG. 9A by following a guidewire 216 that has already been inserted pursuant to the initial operation 900. FIG. 8B shows the lumen body 704 of the catheter 702 in position with the medical leads 218, 220 being inserted through the lumen 706 pursuant to insertion operation 906 once the guidewire 216 and introducer 708 have been removed pursuant to removal operation 904. Once the leads 218, 220 are present in their approximate final location, the catheter 702 is then removed pursuant the removal operation 908, with the medical leads 218, 220 then being in position as shown in FIG. 2E.

Figure 9B:
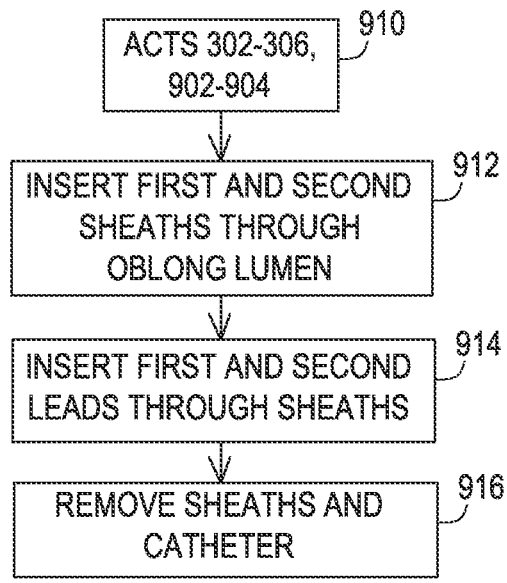
FIG. 9B shows a set of acts that utilize the assembly of FIG. 7B to implant multiple medical leads.

FIG. 8CA shows an assembly including catheter 712 after insertion into the epidural space 210 and removal of the introducer 708 and guidewire 216 in accordance with the initial operation 910 of FIG. 9B. Here, the first and second sheaths 714, 716 are also inserted through the lumen 706 pursuant to the sheath operation 912 and to extend the distal ends of the sheaths 714, 716 beyond the distal end of the catheter 712. This allows the distal ends of the sheaths 714, 716 to deflect into an orientation generally parallel to the spinal cord 212. FIG. 8CB shows the leads 218, 220 being inserted through the sheaths 714, 716 until they reach their approximate final position pursuant to the lead operation 914. The catheter 712 and sheaths 714, 716 are then removed pursuant to the removal operation 916 with the medical leads 218, 220 being in position as shown in FIG. 2E.

Figure 8D:
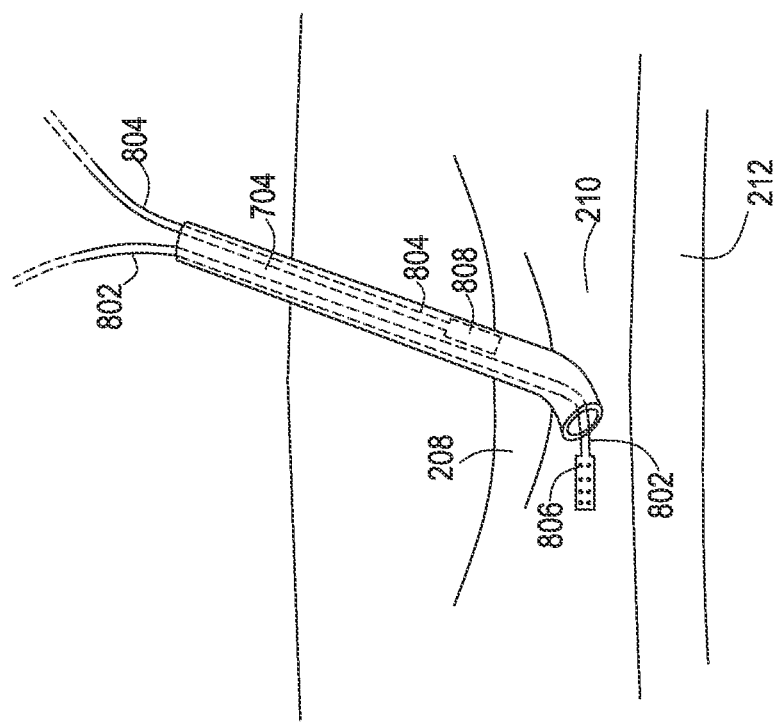
FIGS. 8DA-8DB show a fifth assembly utilizing a lumen with an oblong lateral cross-section during an implantation procedure
Figure 9C:
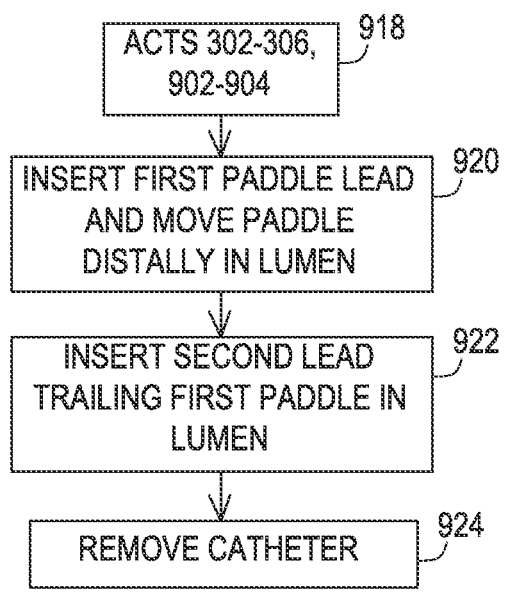
FIG. 9C shows a set of acts that utilize an assembly including multiple paddle medical leads.

FIG. 8DA shows an assembly including catheter lumen body 704 after insertion into the epidural space 210 and removal of the introducer 708 and guidewire 216 in accordance with the initial operation 918 of FIG. 9C. Here, first and second paddle leads 802, 804 are being inserted through the lumen 706 pursuant to the insertion operations 920 and 922. For some embodiments, the width of the paddle 806, 808 may be of a size that is too large for two paddles 806, 808 to be laterally adjacent within the oblong lumen 706. In that case as well as some others, one paddle 806 is inserted first, at insertion operation 920, ahead of the other paddle 808 and moved distally down the catheter lumen body 704. The other paddle 808 is then inserted pursuant to the insertion operation 922 such that the latter paddle 808 is adjacent to only the lead body of the lead 802 where the lead body has a smaller width than the paddle 806. Both leads 802, 804 are fully inserted through the catheter lumen body 704 as shown in FIG. 8DB until reaching their approximate final positions. The catheter 702 is then removed pursuant to the removal operation 924 with the paddle leads 802, 804 being in an approximate final position similar to that shown for percutaneous leads in FIG. 2E.

Figure 10:
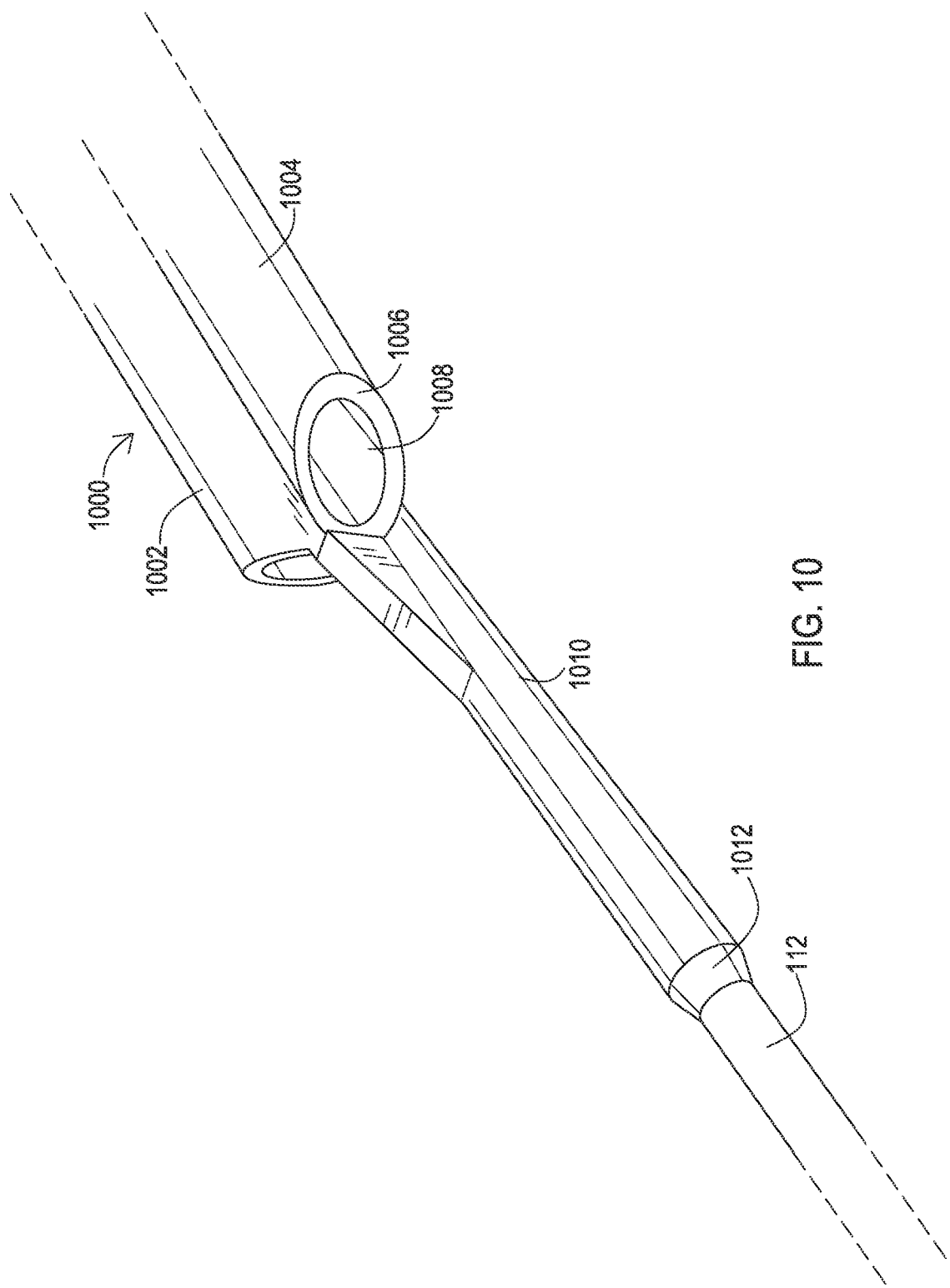
FIG. 10 shows a sixth example of an assembly for implanting multiple medical leads through a single entry by way of a catheter having a central lumen housing a guidewire.

FIG. 10 shows another embodiment of a medical assembly including a catheter 1000. This catheter 1000 includes multiple lumen bodies 1002, 1004 that are integrally formed and may be a unitary structure, each having a lumen 1008. In this particular embodiment, each of the lumen bodies 1002, 1004 has a beveled distal end 1006. Additionally, this embodiment includes a dedicated guidewire lumen body 1010 that is integral with the other lumen bodies and that extends distally beyond the lumen bodies 1002, 1004 and includes a guidewire lumen 1012. The guidewire lumen body 1010 may be made of a flexible material to allow the guidewire lumen body 1010 to deflect as it follows the path of the guidewire 112 upon entering the defined space within the body. A trocar may be positioned in each lumen body 1002, 1004 and may be retracted once the distal end of the lumen bodies 1002, 1004 enter the defined space.

The assembly of FIG. 10 is inserted into the epidural space in the same manner as discussed above for the embodiment of FIG. 1A, utilizing the same approach as illustrated in FIGS. 2A-2E and FIG. 3 except that the dedicated guidewire lumen 1012 receives the guidewire 216 as shown in FIGS. 2B and 2C rather than the guidewire 216 being present within a lumen of the lumen bodies that is used to introduce a medical lead.

Figure 11:
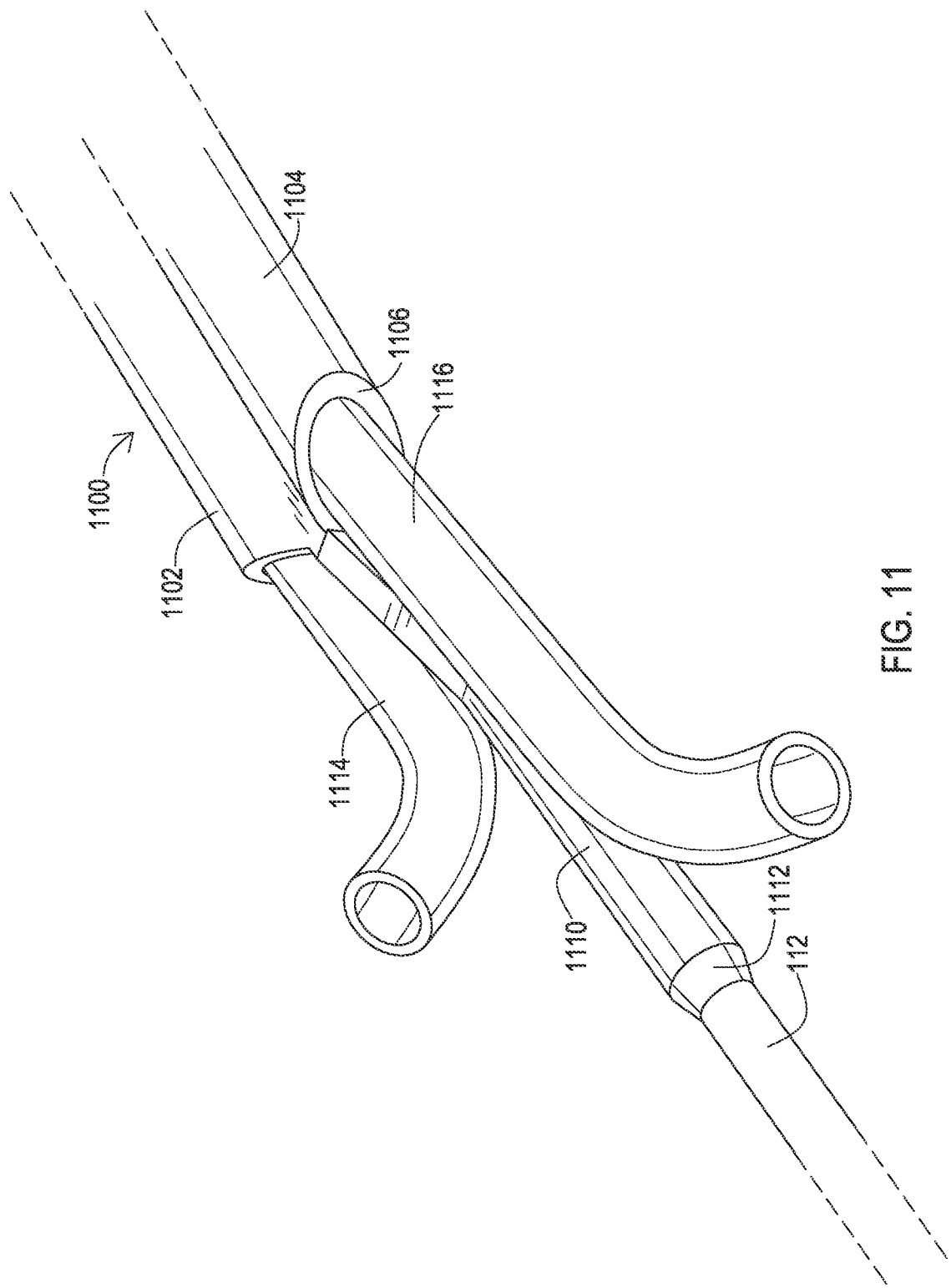
FIG. 11 shows a seventh example of an assembly for implanting multiple medical leads through a single entry by way of a catheter having a central lumen housing a guidewire and having sheaths in lead lumens.

FIG. 11 shows another embodiment of a medical assembly including a catheter 1100. Similar to the catheter 1000 of FIG. 10, this catheter 1100 includes multiple lumen bodies 1102, 1104 that are integrally formed and may be a unitary structure and define lumens 1106. This catheter 1100 also includes a dedicated and deflectable guidewire lumen body 1112 that receives the guidewire 112. However, this assembly also includes sheaths 1114 and 1116 present within the lumens 1106 of the lumen bodies 1102, 1104. The distal ends of these sheaths 1114, 1116 may be deflectable and/or have shape memory as discussed above for the sheaths present in other embodiments.

The assembly of FIG. 11 is inserted into the epidural space in the same manner as discussed above for the embodiment of FIG. 4, utilizing the same approach as illustrated in FIGS. 2A-2C, 5A-5B and FIG. 6 except that the dedicated guidewire lumen 1112 receives the guidewire 216 as shown in FIGS. 2B and 2C rather than the guidewire 216 being present within a lumen of the lumen bodies that is used to introduce a medical lead.

Figure 12:
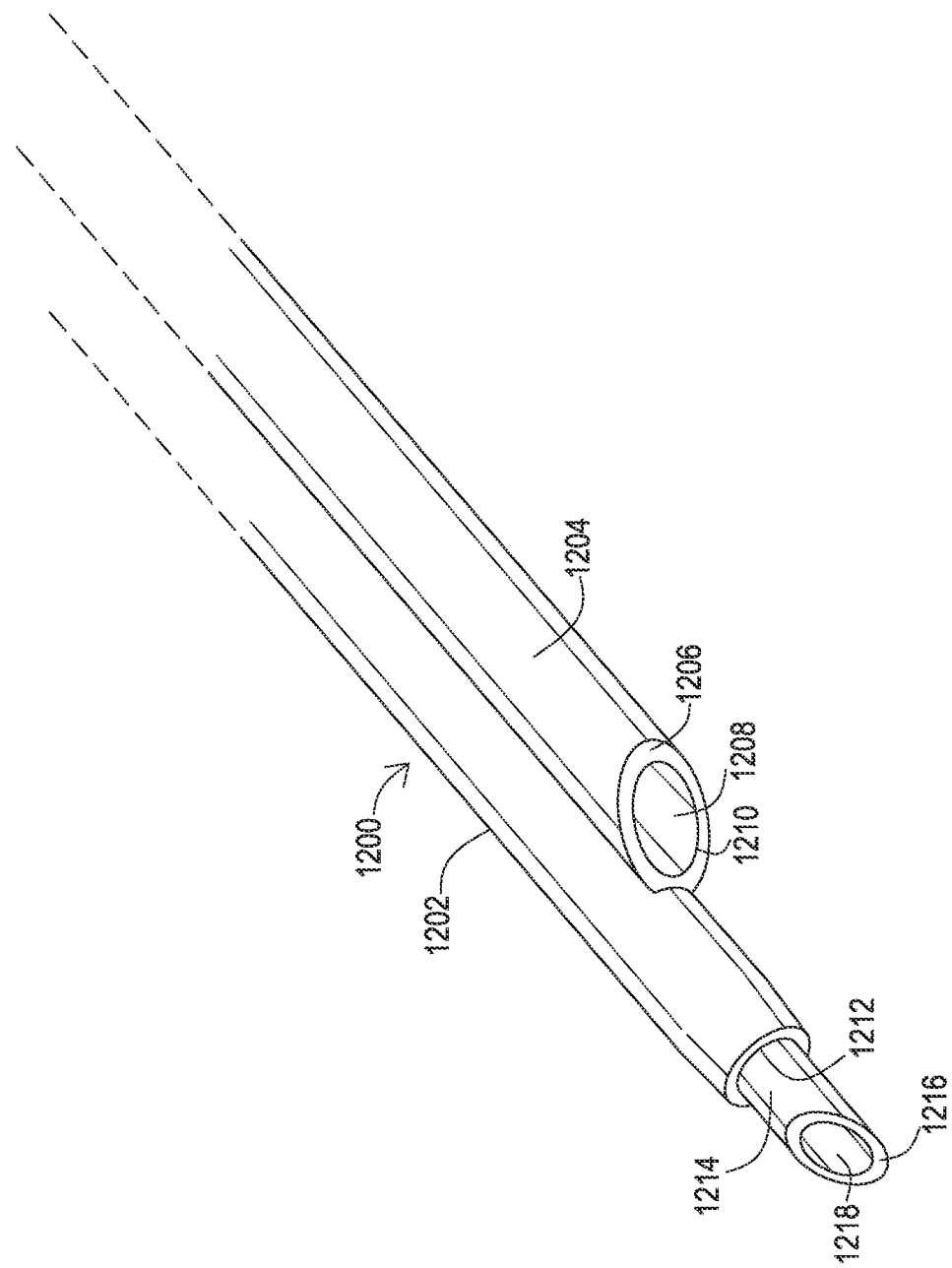
FIG. 12 shows an eighth example of an assembly for implanting multiple medical leads through a single entry by way of a catheter having a lumen housing an implantation needle.

FIG. 12 shows an embodiment of a medical assembly that eliminates the use of a guidewire during insertion. The assembly includes a catheter 1200 that has multiple lumen bodies 1202, 1204 that are integrally formed and may be a unitary structure with each having a lumen 1210, 1212. Each of the lumens 1210, 1212 defined by the lumen bodies 1202, 1204 may be substantially the same diameter. The distal end 1208 of the lumen body 1204 includes a beveled surface 1206 like that of the embodiment of FIG. 1A. However, an insertion needle 1214 is present within the lumen 1212 of the lumen body 1202. In this example, the insertion needle 1214 includes a beveled distal end 1216 having a lumen 1218 that may include a removable trocar for added stiffness and to fill the lumen 1218 during insertion. Further, a trocar may also be present within the lumen 1210 to provide additional stiffness during insertion.

Upon the distal end of the catheter 1200 entering the defined space within the body, the needle 1214 and any trocar within the needle 1214 may be retracted as may any trocar present within the lumen 1210. At this point, the distal end of the catheter 1200 may be deflected, such as by further movement and/or shape memory providing a pre-formed bend.

Figure 13A:
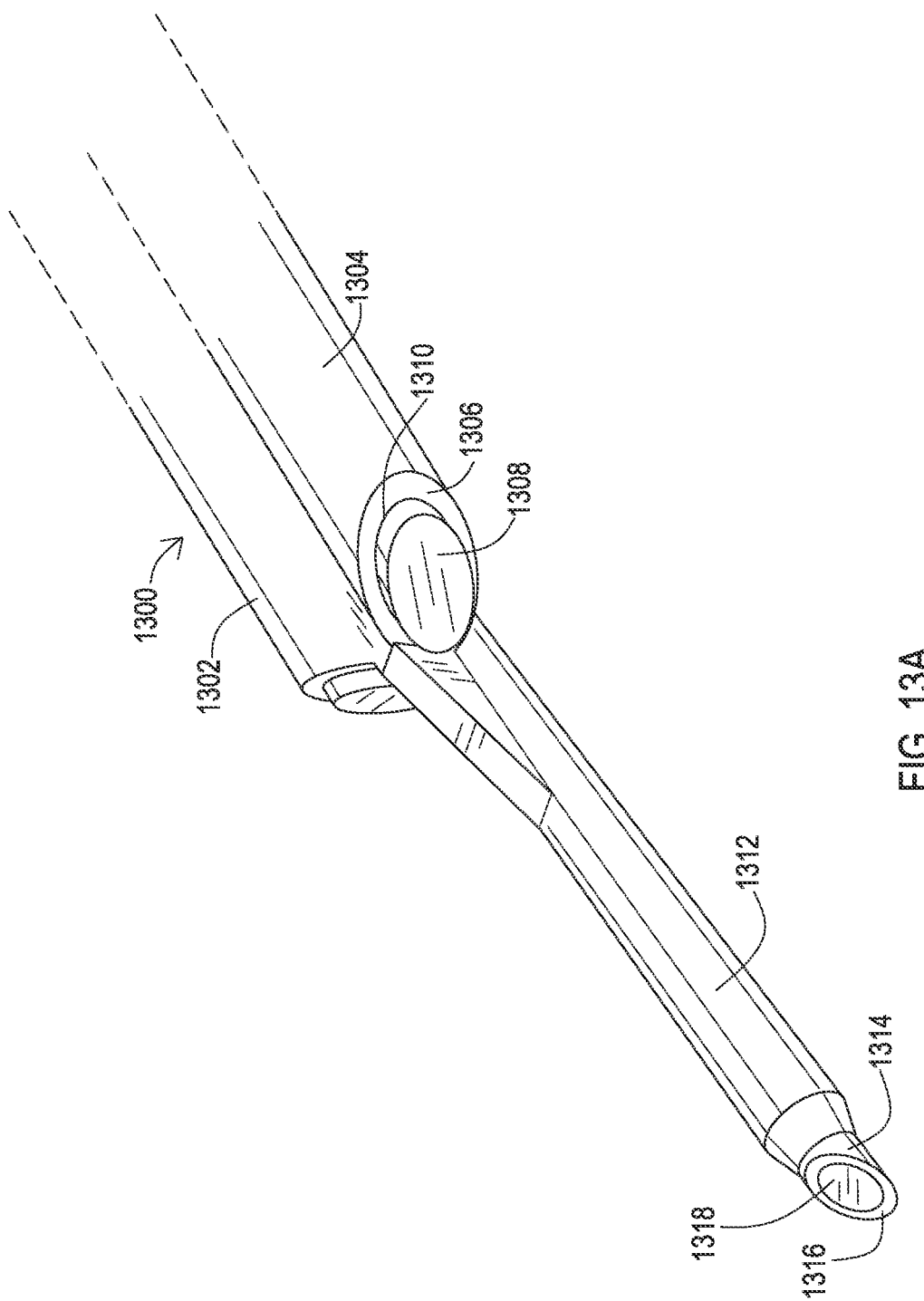
FIG. 13A shows a ninth example of an assembly for implanting multiple medical leads through a single entry by way of a catheter having a central extended lumen housing an implantation needle.

FIG. 13A shows another embodiment of a medical assembly that eliminates the use of a guidewire during insertion. The assembly includes a catheter 1300 that has multiple lumen bodies 1302, 1304 that are integrally formed and may be a unitary structure with lumens 1310 and beveled surfaces 1306 on the distal ends 1308 of each. The catheter 1300 also includes a dedicated and deflectable needle lumen body 1312 that receives the insertion needle 1314. The insertion needle 1314 of this example includes a beveled tip 1316 and may also include a lumen 1318 which may be filled by a trocar during insertion. In this particular example, the dedicated needle lumen body 1312 defines a lumen having a smaller diameter than the lumen defined by the lumen bodies 1302, 1304 that receive the medical leads.

The needle lumen body 1312 of this example extends distally beyond the distal end of the lumen bodies 1302, 1304 that receive the medical leads and may be flexible to deflect and/or may include shape memory so as to achieve a pre-formed bend upon removal of the insertion needle 1314. The multiple lumen bodies 1302, 1304 may also be deflectable and/or include shape memory so as to achieve a pre-formed bend upon removal of trocars present within the lumens 1310 during insertion into the defined space.

Figure 13B:
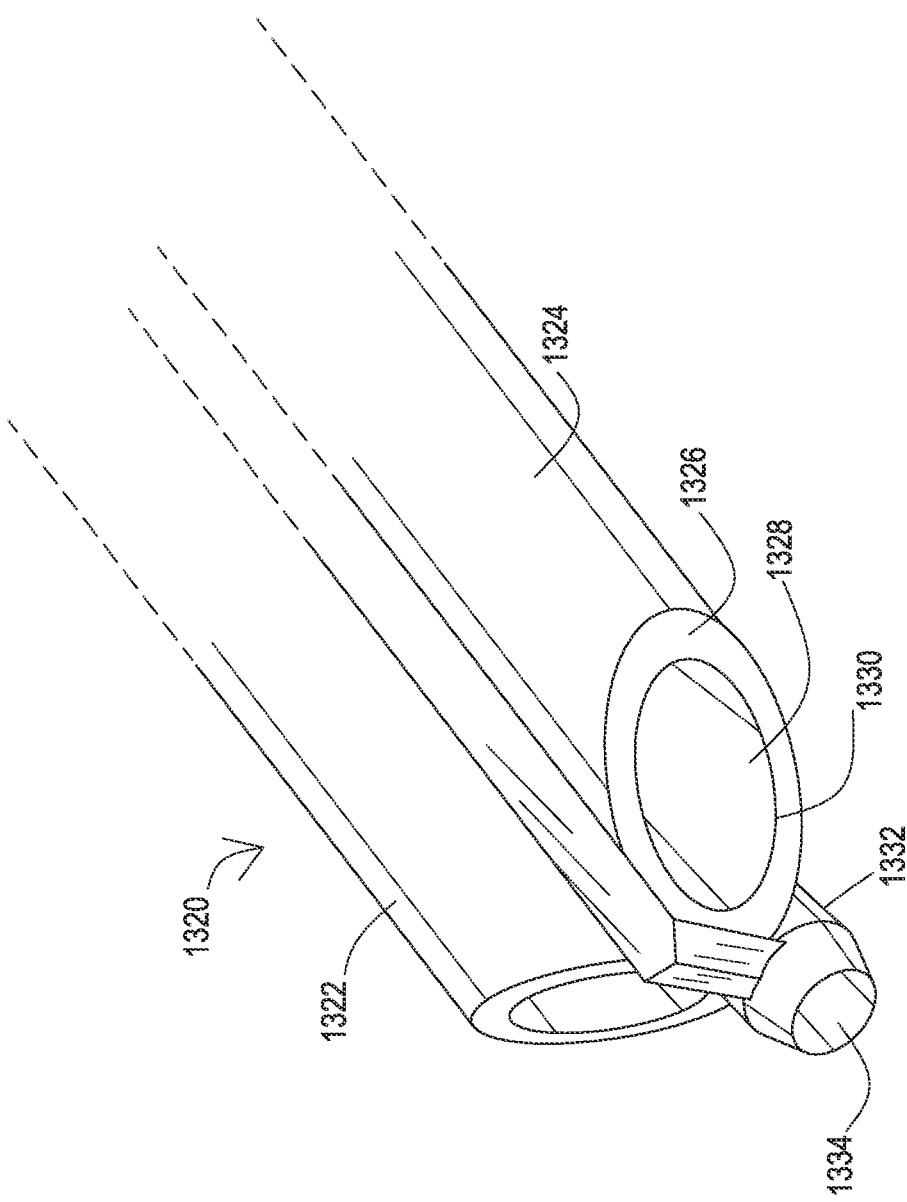
FIG. 13B shows a tenth example of an assembly for implanting multiple medical leads through a single entry by way of a catheter having a central non-extended lumen housing an implantation needle.

FIG. 13B shows another embodiment of a medical assembly like that of FIG. 10 or 13A except that a dedicated lumen body 1332 of a catheter 1320 terminates at or near the distal end of multiple lumen bodies 1322, 1324 rather than extending farther distally. The dedicated lumen body 1332 may be for purposes of receiving a guidewire where the catheter 1320 is inserted in the same manner as the catheter 1000 of FIG. 10 or may be for purposes of receiving an insertion needle where the catheter 1320 is inserted in the same manner as the catheter 1300 of FIG. 13A. In either case, the distal end of the catheter may be flexible so as to be deflectable and/or may include shape memory to establish a pre-formed bend. In this example, the dedicated lumen body 1332 defines a lumen 1334 that has a smaller diameter than the lumen of the other lumen bodies.

Figure 14A:
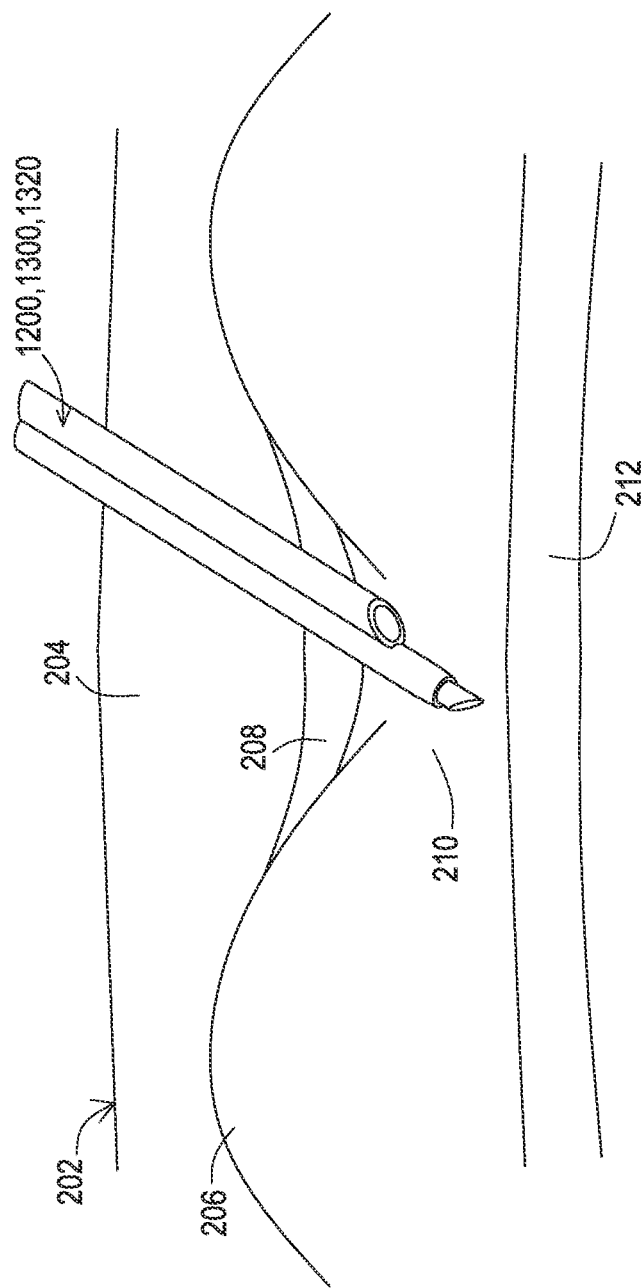

FIGS. 14A-14C show a series of phases of the multi-lumen catheter embodiments of FIGS. 12-13B being inserted without the use of a guidewire and also show the implantable medical leads ultimately being inserted into the defined space. While the catheter 1200 of FIG. 12 is specifically illustrated, it will be appreciated that the same phases and operations are also applicable to the catheters 1300 and 1320.

Figure 15:
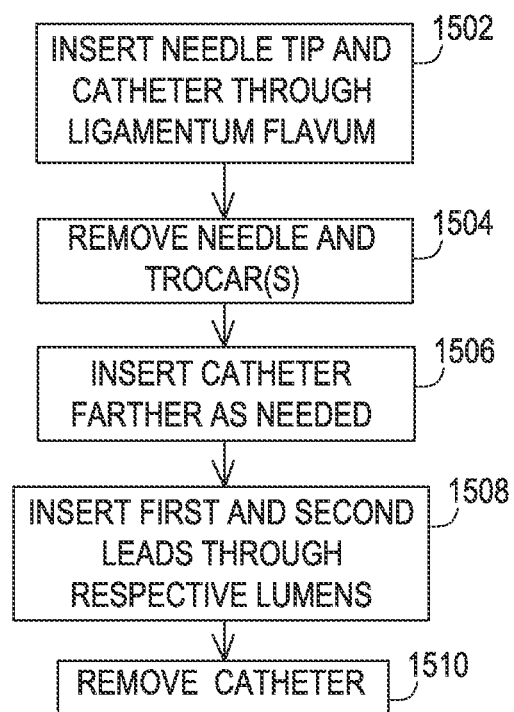
FIG. 15 shows a set of acts that utilize the assembly of FIG. 12 to implant multiple medical leads.

As with the discussion above in the various figures showing phases of insertion, these phases are illustrated and discussed with reference to implantation into the epidural space of a body. However, it will be appreciated that the assemblies and techniques may also be applicable to other defined spaces within a body. FIG. 15 shows a series of acts taken to progress through the phases of FIGS. 14A-14C. Additionally, while a hub is not shown on a proximal end of the needle and catheter combination, it will be appreciated that a hub may be present to allow insertion and removal of the various objects.

FIG. 14A shows the assembly including the catheter 1200 and the insertion needle 1214 being inserted into a body 202 by passing the assembly including the catheter 1200 and insertion needle 1214 through the skin 204 and through the ligamentum flavum 208, adjacent vertebral bones 206 pursuant to the needle operation 1502 of FIG. 15. The needle 1214 enters the epidural space 210 but care is exercised to avoid contact with the dura or any other layers about the spinal cord 212. The needle 1214 and any trocars may then be removed from the needle 1214 and catheter 1200 pursuant to removal operation 1504 to allow the distal end of the catheter to deflect and/or if applicable achieve a pre-formed bend. The catheter 1200 is inserted further as the deflection occurs pursuant to insertion operation 1506 to reach the position as shown in FIG. 14B.

FIG. 14C then shows first and second implantable medical leads 218, 220 being inserted through each lumen of the catheter 1200 so that the medical leads 218, 220 are then directed into the epidural space and in a direction largely parallel to the spinal cord 212 and pursuant to an insertion operation 1508. Once the medical leads 218, 220 have reached an approximate final position within the epidural space 210, the catheter 1200 is then removed pursuant to a removal operation 1510 to leave the medical leads 218, 220 in position within the epidural space 210 as shown in FIG. 2E.

Figure 16:
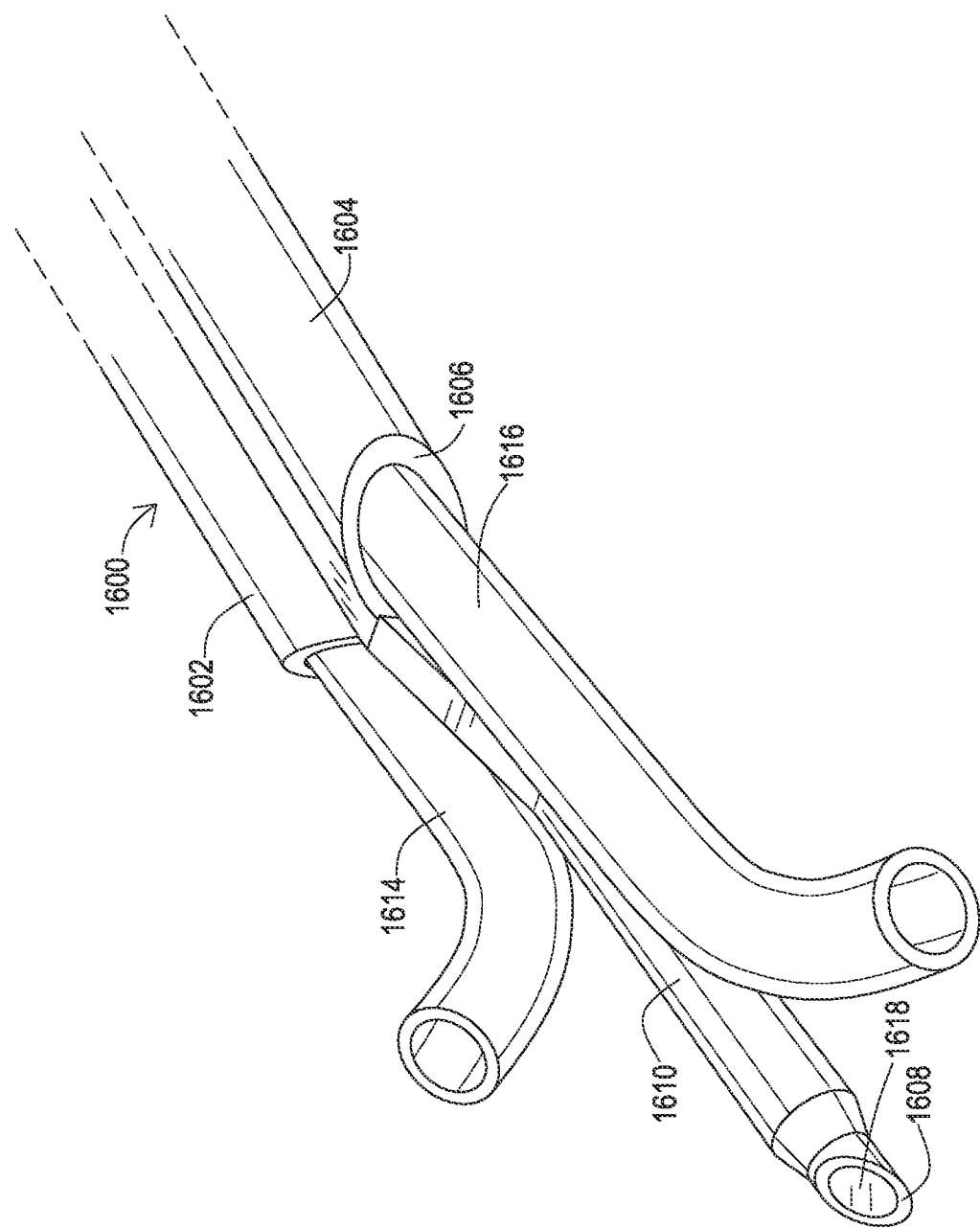
FIG. 16 shows an eleventh example of an assembly for implanting multiple medical leads through a single entry by way of a catheter having a central lumen housing an implantation needle while including sheaths in other lumens.

FIG. 16 shows another embodiment of a medical assembly including a catheter 1600 where a guidewire is not used for insertion. This assembly is similar to that of FIG. 13A except that sheaths 1614 and 1616 are present within the lumens 1606 of lumen bodies 1602 and 1604 where these lumen bodies are integrally formed and may be a unitary structure. These sheaths 1614, 1616 may be deflectable and or have a shape memory providing a pre-formed bend as discussed above for the sheaths of other embodiments. The catheter 1600 includes a dedicated needle lumen body 1610 and a needle tip 1608 extends from the needle lumen body 1610. Where the needle tip 1608 includes a lumen, a trocar 1618 may be present to fill the lumen during insertion. In this example, the dedicated needle lumen body 1610 defines a lumen that has a smaller diameter than the lumen of the other lumen bodies.

It will be appreciated that variations to the catheter 1600 are appropriate for other embodiments that also utilize a needle in a lumen to avoid using a guidewire. For instance, the assembly of FIG. 12 may include sheaths like those of FIG. 16 during the insertion process once the needle 1214 and any trocars are removed. Similarly, sheaths may be used within the assemblies of FIGS. 13A and 13B.

FIGS. 17A-17B show a series of phases of the multi-lumen catheter embodiment of FIG. 16 being inserted without the use of a guidewire and also show the implantable medical leads ultimately being inserted into the defined space. While the catheter 1600 of FIG. 16 is specifically illustrated, it will be appreciated that the same phases and operations are also applicable to the catheters 1200, 1300, and 1320 where those assemblies utilize sheaths during the lead implantation process.

Figure 18:
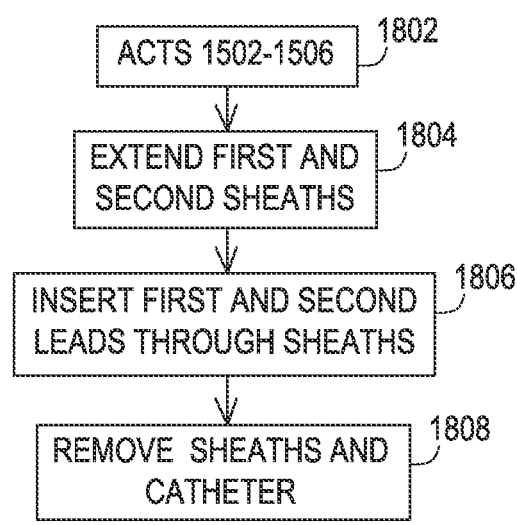
FIG. 18 shows a set of acts that utilize the assembly of FIG. 16 to implant multiple medical leads.

FIG. 17A shows a phase that occurs after the catheter 1600 has been inserted into the defined space and the insertion needle and any trocars have been removed from the catheter 1600 pursuant to initial operation 1802 of FIG. 18. Additionally, the needle lumen 1610 has deflected, and the first and second sheaths 1614, 1616 have been inserted and extended through the catheter 1600 until the distal ends of the sheaths 1614, 1616 exit from the catheter and deflect pursuant to the sheath operation 1804. As shown in FIG. 17B, the first and second leads 218, 220 are then inserted through the sheaths 1614, 1616 until entering the epidural space and reaching an approximate final position pursuant to insertion operation 1806. The catheter 1600 and sheaths 1614, 1616 are then removed pursuant to the removal operation 1808 while the leads 218, 220 remain in their approximate final position such as that shown in FIG. 2E.

Figure 19:
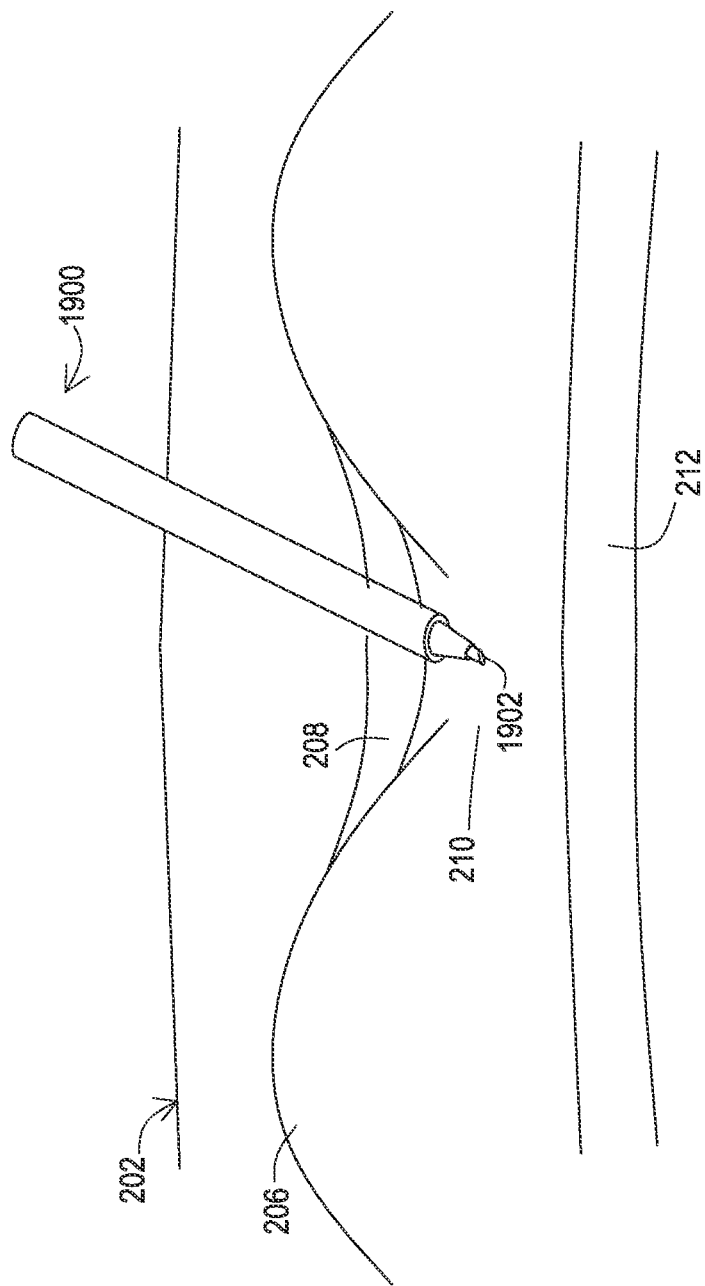
FIG. 19 shows an assembly like that of FIG. 7A during an alternative implantation procedure.
Figure 20A:
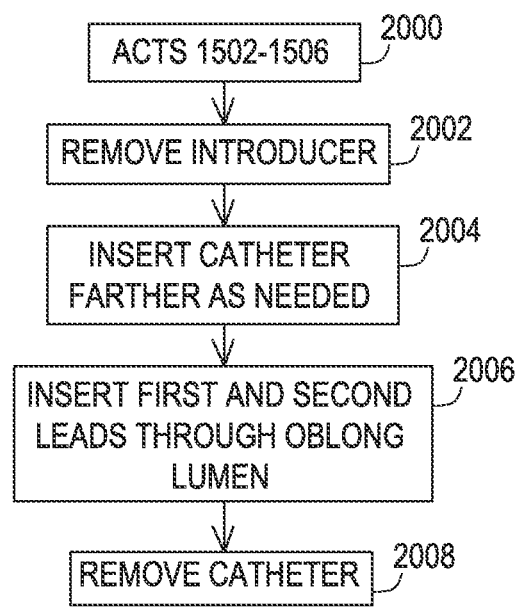
FIG. 20A shows a set of acts that utilize the assembly of FIG. 7A during the alternative implantation procedure for implanting multiple medical leads.

FIG. 19 shows a medical assembly including a catheter 1900 being inserted into the epidural space 210. This assembly is the same as that of FIG. 7A except that an insertion needle 1902 is present within the lumen of the introducer that is present within the lumen of the catheter 1900 such that a guidewire is not used during insertion. The catheter 1900 is inserted into the epidural space pursuant to the initial operation 2000 of FIG. 20A which includes inserting the catheter 1900, then removing the insertion needle. Additionally, the introducer is also removed at the removal operation 2002 which may occur in unison with removal of the needle.

In one embodiment, the catheter 1900 is inserted further as needed as in insertion operation 2004, such as shown in FIG. 8B, until the distal end of the catheter 1900 has deflected or established a pre-formed bend within the epidural space. The first and second leads 218, 220 are then inserted through the catheter 1900 until reaching an approximate final position within the epidural space 210 pursuant to the insertion operation 2006. The catheter 1900 is then removed in a removal operation 2008 with the leads being in the approximate final position as shown in FIG. 2E.

Figure 20B:
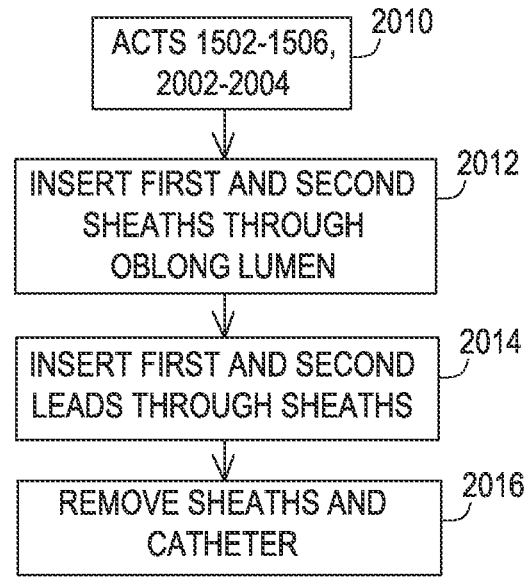
FIG. 20B shows a set of acts that utilize the assembly of FIG. 7B during the alternative implantation procedure for implanting multiple medical leads.

In another embodiment such as where the catheter 1900 utilizes sheaths similar to that shown in FIG. 7B, once the catheter 1900 has been inserted with an insertion needle in the lumen of the introducer within the catheter 1900, then the needle and introducer are removed pursuant to the initial operation 2010 of FIG. 20B. Then, first and second sheaths are inserted through the oblong lumen in a sheath operation 2012 until the distal end of the sheaths enter the epidural space and then deflect into an appropriate position as shown in FIG. 8CA. First and second medical leads are then inserted through the sheaths until reaching an approximate final position pursuant to insertion operation 2014 and as shown in FIG. 8CB. The catheter 1900 and sheaths are then removed in a removal operation 2016 with the leads being in the approximate final position as shown in FIG. 2E.

Figure 20C:
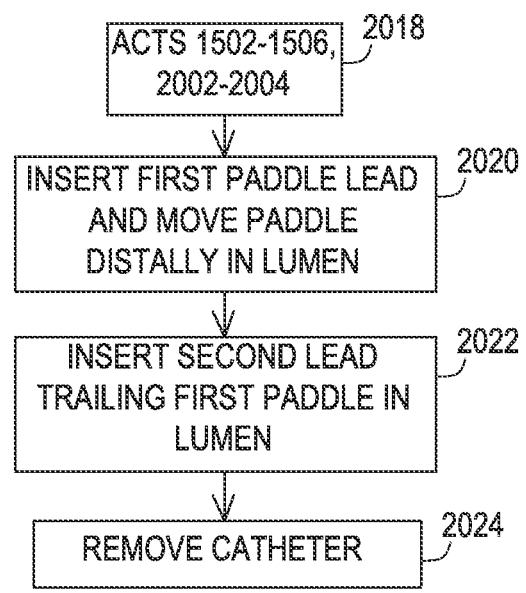
FIG. 20C shows a set of acts that utilize the assembly of FIG. 7A during the alternative implantation procedure for implanting multiple medical leads where at least one is a paddle lead.

In another embodiment such as where the catheter 1900 is used to implant at least one paddle lead, once the catheter 1900 has been inserted with an insertion needle in the lumen of the introducer, then the needle and introducer are removed pursuant to the initial operation 2018 of FIG. 20C. For embodiments where the oblong lumen of the catheter can accommodate one paddle and one lead body and where two paddle leads are being implanted, then the first paddle lead is inserted into the oblong lumen and moved distally in a paddle operation 2020 and as shown in FIG. 8DA. Then, the second paddle lead is inserted trailing the first paddle in the oblong lumen so that the second paddle is laterally adjacent to the lead body of the first paddle lead in a paddle operation 2022 and as shown in FIG. 8DB. Once the paddle leads have reached an approximate final position within the epidural space, then the catheter 1900 is removed in a removal operation 2024 with the paddle leads being in the approximate final position similar to that shown for percutaneous leads in FIG. 2E.

While embodiments have been particularly shown and described, it will be understood by those skilled in the art that various other changes in the form and details may be made therein without departing from the spirit and scope of the invention.

What is claimed is:

1. A medical assembly comprising:
   two medical leads having distal electrodes;
   a multiple lumen catheter configured to insert the two medical leads through a single opening to a defined space within a patient and further configured to be removed while the two medical leads remain inserted for subsequent delivery of stimulation pulses by the distal electrodes to the defined space, wherein the multiple lumen catheter comprises a distal end with a pre-formed bend, wherein the multiple lumen catheter comprises at least two lumen bodies; and
   trocar present within a lumen of a first lumen body of the multiple lumen catheter, the trocar being positioned within the lumen at the distal end of the multiple lumen catheter such that the pre-formed bend is held straight.

2. The medical assembly of claim 1, wherein a guidewire is present within a lumen of a second lumen body of the multiple lumen catheter.

3. The medical assembly of claim 1, wherein the multiple lumen catheter comprises a shape memory material.

4. The medical assembly of claim 1, wherein the pre-formed bend of the multiple lumen catheter is achieved once the trocar is removed from the first lumen body of the catheter.

5. The medical assembly of claim 1, the trocar includes a flexible region between a distal end and a proximal end of the trocar.

6. A medical assembly, comprising:
   two medical leads having distal electrodes;
   a multiple lumen catheter configured to insert the two medical leads through a single opening to a defined space within a patient and further configured to be removed while the two medical leads remain inserted for subsequent delivery of stimulation pulses by the distal electrodes to the defined space, wherein the multiple lumen catheter comprises a distal end with a pre-formed bend, wherein the multiple lumen catheter comprises at least two lumen bodies; and
   a guidewire present within a lumen of a first lumen body of the multiple lumen catheter.

7. The medical assembly of claim 6, wherein the multiple lumen catheter comprises a shape memory material.

8. The medical assembly of claim 6, wherein a trocar is present within a lumen of a second lumen body of the multiple lumen catheter, the trocar being positioned within the lumen at the distal end of the catheter to hold the multiple lumen catheter straight.

9. The medical assembly of claim 8, wherein the multiple lumen catheter has the pre-formed bend once the trocar is removed from the lumen of the second lumen body.

10. A medical assembly comprising:
    two medical leads having distal electrodes;
    a multiple lumen catheter configured to insert the two medical leads through a single opening to a defined space within a patient and further configured to be removed while the two medical leads remain inserted for subsequent delivery of stimulation pulses by the distal electrodes to the defined space, wherein the multiple lumen catheter comprises a distal end with a pre-formed bend, wherein the multiple lumen catheter comprises at least two lumen bodies;
    a trocar present within a first lumen body of the multiple lumen catheter, the trocar being positioned within the lumen at the distal end of the multiple lumen catheter such that the pre-formed bend is held straight; and
    a guidewire present within a second lumen body of the catheter.

11. The medical assembly of claim 10, wherein the multiple lumen catheter comprises a shape memory material.

12. The medical assembly of claim 10, the trocar includes a flexible region between a distal end and a proximal end of the trocar.

13. The medical assembly of claim 10, wherein the multiple lumen catheter has the pre-formed bend once the trocar is removed from the lumen of the second lumen body.

* * * * *